United States Patent
Kang et al.

(10) Patent No.: US 11,254,963 B2
(45) Date of Patent: Feb. 22, 2022

(54) INCREASING ORNITHINE ACCUMULATION TO INCREASE HIGH MANNOSE GLYCOFORM CONTENT OF RECOMBINANT PROTEINS

(71) Applicant: Amgen Inc., Thousand Oaks, CA (US)

(72) Inventors: Sohye Kang, Camarillo, CA (US); Chung Huang, Jr., Newbury Park, CA (US); Hedieh Barkhordarian, Newbury Park, CA (US); Pavel Bondarenko, Thousand Oaks, CA (US); Zhongqi Zhang, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 16/676,340

(22) Filed: Nov. 6, 2019

(65) Prior Publication Data

US 2020/0071738 A1    Mar. 5, 2020

Related U.S. Application Data

(62) Division of application No. 15/111,470, filed as application No. PCT/US2014/069378 on Dec. 9, 2014, now Pat. No. 10,513,723.

(60) Provisional application No. 61/926,481, filed on Jan. 13, 2014.

(51) Int. Cl.
*C12P 21/00* (2006.01)
*C07K 16/00* (2006.01)
*C12N 1/38* (2006.01)
*C07K 14/52* (2006.01)
*C12N 5/071* (2010.01)

(52) U.S. Cl.
CPC ............ *C12P 21/005* (2013.01); *C07K 14/52* (2013.01); *C07K 16/00* (2013.01); *C12N 1/38* (2013.01); *C12N 5/0682* (2013.01); *C07K 2317/14* (2013.01); *C07K 2317/41* (2013.01); *C12N 2500/32* (2013.01); *C12N 2500/33* (2013.01); *C12N 2500/46* (2013.01); *C12N 2500/90* (2013.01); *C12N 2510/02* (2013.01); *C12N 2521/00* (2013.01)

(58) Field of Classification Search
None
See application file for complete search history.

(56) References Cited

U.S. PATENT DOCUMENTS

| | | |
|---|---|---|
| 4,695,623 A | 9/1987 | Stabinsky |
| 4,897,471 A | 1/1990 | Stabinsky |
| 4,968,607 A | 11/1990 | Dower et al. |
| 5,075,222 A | 12/1991 | Hannum et al. |
| 5,149,792 A | 9/1992 | Thomason |
| 5,272,064 A | 12/1993 | Thomason |
| 5,395,760 A | 3/1995 | Smith et al. |
| 5,610,279 A | 3/1997 | Brockhaus et al. |
| 5,721,121 A | 2/1998 | Etcheverry et al. |
| 5,767,064 A | 6/1998 | Sims et al. |
| 5,856,296 A | 1/1999 | Mosley et al. |
| 5,981,713 A | 11/1999 | Colotta et al. |
| 6,015,938 A | 1/2000 | Boyle et al. |
| 6,096,728 A | 8/2000 | Collins et al. |
| 6,204,363 B1 | 3/2001 | Zsebo et al. |
| 6,235,883 B1 | 5/2001 | Jakobovits et al. |
| 6,271,349 B1 | 8/2001 | Dougall et al. |
| 6,337,072 B1 | 1/2002 | Ford et al. |
| 6,544,424 B1 | 4/2003 | Shevitz |
| 8,053,238 B2 | 11/2011 | Jin et al. |
| 2003/0104996 A1* | 6/2003 | Li ........................ A61K 47/20 514/7.7 |

FOREIGN PATENT DOCUMENTS

| | | |
|---|---|---|
| EP | 0367566 B1 | 5/1997 |
| EP | 0460846 B1 | 2/2002 |
| WO | WO 1994/10308 A1 | 5/1994 |
| WO | WO 1997/01633 A1 | 1/1997 |
| WO | WO 2001/36637 A1 | 5/2001 |
| WO | WO 2008/154014 A2 | 12/2008 |
| WO | WO 2012/145682 A1 | 10/2012 |
| WO | WO 2013/006479 A2 | 1/2013 |

OTHER PUBLICATIONS

Daune et al. Biochem J. Jul. 15, 1988; 253(2): 481-488. (Year: 1988).*
Koomoa et al. Cancer Res. Dec. 1, 2008;68(23):9825-31. (Year: 2008).*
Hölttä et al. Biochim Biophys Acta. Dec. 30, 1982;721(4):321-7. Abstract. (Year: 1982).*
Terayam et al. Biochim Biophys Acta. Apr. 29, 1982;720(2):188-92. (Year: 1982).*
Alcazar et al., Involvement of polyamines in plant response to abiotic stress, Biotechnol. Lett. (2006) 28:1867-1876.
Axelsson et al., Neutralization of pH in the Golgi Apparatus Causes Redistribution of Glycosyltransferases and Changes in the O-Glycosylation of Mucins, *Glycobiology* (2001), 11(8):633-644.
Berkowitz et al., Arginase Reciprocally Regulates Nitric Oxide Synthase Activity and Contributes to Endothelial, Circulation (2003), 108(16):2000-2006.
Camacho et al., Hyperornithinaemia-Hyperammonaemia-Homocitrullinuria Syndrome is Caused by Mutations in a Gene Encoding a Mitochondrial Ornithine Transporter, *Nature Genetics* (1999), 22:151-158.
Campbell et al., Ornithine Transcarbamylase Deficiency: A Cause of Lethal Neonatal Hyperammonemia in Males, *NJM* (1973), 288(1):1-6.

(Continued)

*Primary Examiner* — Christian L Fronda
(74) *Attorney, Agent, or Firm* — Henry P. Wu

(57) ABSTRACT

The present invention relates to a method for manipulating the high mannose glycoform content of recombinant glycoproteins by regulating ornithine metabolism during cell culture.

16 Claims, 11 Drawing Sheets

(56) References Cited

OTHER PUBLICATIONS

Daune et al., 5-Fluromethylornithine, an Irreversible and Specific Inhibitor of L-Ornithine; 2-oxo-acid Aminotransferase, *Biochem J.* (1988), 253:481-488.
Do et al., Mechanism of BLyS Action in B Cell Immunity, *Cytokine Growth Factor Rev.* (2002), 13:1; 19-25.
Furey, Scale-Up of a Cell Culture Perfusion Process—A Low-Shear Filtration System that Inhibits Filter-Membrane Fouling, *Gen. Eng. News* (2002) 22:7; 62-63.
Goetze et al., High-Mannose Glycans in the Fc Region of Therapeutic IgG Antibodies Increase Serum Clearance in Humans, *Glycobiology*, (2011) 21:7:949-959.
Graham et al., Characteristics of a Human Cell Line Transformed by DNA from Human Adenovirus Type 5, *J. Gen. Virol.* (1977) 36:59-72.
Hakansson et al., Crystal Structure of the Trimeric α-Helical Coiled-Coil and the Three Lectin Domains of Human Lung Surfactant Protein D, *Structure* (1999), 7:255-64.
Harbury et al., a Switch Between Two-, Three-, and Four-Stranded Coiled Coils in GCN4 Leucine Zipper Mutants, *Science* (1993), 262:1401-05.
Harbury et al., Crystal Structure of an Isoleucine-Zipper Trimer, *Nature* (1994), 371:80-83.
Hendrick et al., Increased Productivity of Recombinant Tissular Plasminogen Activator (t-PA) by Butyrate and Shift of Temperature: A Cell Cycle Phases Analysis, *Cytotechnology*, Kluwer Academic Publishers (2001) 36:1-3:71-83.
Hopkins et al., Hyperammonaemia Due to Ornithine Transcarbamylase Deficiency, *Archive Disease in Childhood* (1969) 44(234):143-148.
Kolhekar et al., Peptidylglycine α-Hydroxylating Monooxygenase: Active Site Residues, Disulfide Linages, and a Two-Domain Model of the Catalytic Core, *Biochemistry* (1997) 36:10901-10909.
Lovejoy et al., Crystal Structure of a Synthetic Triple-Stranded α-Helical Bundle, *Science* (1993), 259:1288-1293.
Maisonpierre et al., Angiopoietin-2, a Natural Antagonist for Tie2 that Disrupts in vivo Angiogenesis, *Science* (1997), 277(5322):55-60.
Mather, Culture of Testicular Cells in Hormone-Supplemented Serum-Free Medium, *Annals NY Acad. Sci.* (1982), 383:44-68.
Mather, Establishment and Characterization of Two Distinct Mouse Testicular Epithelial Cell Lines, *Biol. Reprod.* (1980), 23:243-251.
Matsui et al., Effect of Sodium Butyrate on Induction of Orinthine Decarboxylase Activity in Phytohemagglutinin-Stimulated Lymphocytes, *Chemico-Biological Interactions*, Elsevier Science Irland (1984) 51:2:141-149.
Michell et al., Osmotic Stress Induces Variation in Cellular Levels of Ornithine Decarboxylase-Antizyme (1998), 329:453-459.
Mühling et al., Conscientious Metablic Monitoring on a Patient with Hyperornithinemia-Hyperammonemia-Homocitrullinuria (HHH) Syndrome Undering Anaesthesia, *Amino Acids* (2001), 21(3):303-318.
Munro et al., Effects of External Osmolality on Polyamine Metabolism in HeLa Cells, *BBA* (1975), 411(2):263-281.
NCBI Accession No. NM_006682.
Pacis et al., Effects of Cell Culture Conditions on Antibody N-Linked Glycosylation—What Affects High Mannose 5 Glycoform, *Biotechnol Bioeng* (2011), 108:2348-2358.
Park et al., Expression of Carbomoyl Phosphate Synthetase I and Ornithine Transcarbamoylase Genes in Chinese Hamster Ovary dhfr-Cells Decreases Accumulation of Ammonium Ion in Culture Media, *J. Biotechnol* (2000), 81(2):129-140.
Pegg, Regulation of Ornithine Decarboxylase, *JBC* (2006), 281(21):14529-14532.
Prasad and Sinha, Effect of Sodium Butyrate on Mammalian Cells in Culture: A Review, *In Vitro* (1976), 12(2):125-132.
Ren et al., An improved trypsin digestion method minimizes digestion-induced modifications on proteins, *Anal. Biochem.* (2009) 392:12-21.
Rivinoja et al., Elevated Golgi pH Impairs Terminal N-Glycosylation by Inducing Mislocalization of Golgi Glycosyltransferases, *J. Cell Physiol.* (2009), 220(1):144-154.
Rüegg et al., Sequence of Human Transcript Expressed in T-Lymphocytes and Encoding a Fibrinogen-Like Protein, *Gene* (1995)160:257-262.
Stettler, et al., New Disposable Tubes for Rapid and Precise Biomass Assessment for Suspension Cultures of Mammalian Cells, *Biotechnol Bioeng.* (2006) 95(6):1228-33.
Takki et al., Genetic Aspects in Gyrate Atrophy of the Choroid and Retina with Hyperornithinaemia, *Br J Ophthalmol* (1974), 58(11):907-916.
Tohyama et al., Mechanisms of Dramatic Fluctuations of Ornithine Decarboxylase Activity upon Tonicity Changes in Primary Cultured Rat Hepatocytes, *Eur J Biochem* (1991), 202(3):1327-1331.
Urlaub et al., Isolation of Chinese Hamster Cell Mutants Deficient in Dihydrofolate Reductase Activity, *Proc Natl Acad Sci USA* (1980) 77: 4216-4220.
Urlaub, Chasin et al., Effect of Gamma Rays at the Dihydrofolate Reductase Locus; Deletions and Inversions, *Somatic Cell and Molecular Genetics* (1986), 12:555-556.
Valle et al., The Hyperornithinemias, *Amino Acids* (2001), 1857-1896.
Vissers et al., Inhibition of Ornithine Carbamoyltransferase by Arginase among Yeasts; Correlation with Energy Production, Subcellular Localization and Enzyme Synthesis, *J. Gen. Microbio.* (1982), 128:1235-1247.
Voisard et al., Potential of Cell Retention Techniques for Large-Scale High Density Perfusion Culture of Suspended Mammalian Cells, *Biotechnol. Bioeng.* (2003), 82:751-765.
Wang et al., Correction of Ornithine Accumulation Prevents Retinal Degeneration in a Mouse Model of Gyrate Atrophy of the Choroid and Retina, *PNAS* (2000), 97(3):1224-1229.
Weekes et al., Inhibition by putrescine of the induction of epidermal ornithine decarboxylase activity and tumor promotion caused by 12-O-tetrade canoyphorbol-13-acetate, *Cancer Research* (1980), 40(11):4013-4018.
Yu et al., Production, Characterization and Pharmacokinetic Properties of Antibodies with N-Linked Mannose-5 Glycans, *MAbs* (2012), 4:475-487.
Zanatta et al., Disturbance of Redox Homeostasis by Ornithine and Homocitrulline in Rat Cerebellum: A Possible Mechanism of Cerebellar Dysfunction in HHH Syndrome, *Life Sciences* (2013), 93(4):161-168.
Zhang, Large-Scale Identification and Quantification of Covalent Modifications in Therapeutic Proteins, *Analytical Chemistry* (2009), 81:8354-8364.

\* cited by examiner

A

B

C

INCREASING ORNITHINE ACCUMULATION TO INCREASE HIGH MANNOSE GLYCOFORM CONTENT OF RECOMBINANT PROTEINS

This application is a divisional of pending U.S. application Ser. No. 15/111,470, filed on Jul. 13, 2016; which is a 371 of International Patent Application No. PCT/US14/069378, filed Dec. 9, 2014; which claims the benefit of U.S. Provisional Application No. 61/926,481 filed Jan. 13, 2014, each of which is incorporated by reference herein.

BACKGROUND OF INVENTION

A variety of post-translational modifications including methylation, sulfation, phosphorylation, lipid addition and glycosylation are performed by higher eukaryotes. Many of the secreted proteins, membrane proteins and proteins targeted to vesicles or certain intracellular organelles are known to be glycosylated. Glycosylation, the covalent attachment of sugar moieties to specific amino acids, is one of the most common, yet important post-translational modifications for recombinant proteins. Protein glycosylation has multiple functions in the cell including its essential role in protein folding and quality control, molecular trafficking and sorting, and cell surface receptor interaction.

N-linked glycosylation involves addition of oligosaccharides to an asparagine residue found in certain recognition sequences in proteins (e.g., Asn-X-Ser/Thr). N-linked glycoproteins contain standard branched structures which are composed of mannose (Man), galactose, N-acetylglucosamine and neuramic acids. High-mannose oligosaccharides typically include two N-acetylglucosamines with multiple mannose residues (5 or more). Glycoproteins produced in mammalian cell culture may contain varied levels of these high mannose (HM or HMN) glycoforms such as Mannose5 (Man5), Mannose6 (Man6), Mannose7 (Man7), Mannose8 (Man8) and Mannose9 (Man9).

While the glycoforms of a recombinant glycoprotein expressed by Chinese hamster ovary (CHO) host cell are largely determined by intrinsic genetic factors, high mannose glycoform content can also be affected by cell culture conditions (Pacis, et al., (2011) *Biotechnol Bioeng* 108, 2348-2358).

Glycosylation can affect therapeutic efficacy of recombinant protein drugs. The influence of glycosylation on bioactivity, pharmacokinetics, immunogenicity, solubility and in vivo clearance of therapeutic glycoproteins have made monitoring and control of glycosylation a critical parameter for biopharmaceutical manufacturing. The high mannose glycoform content of therapeutic proteins is a critical quality attribute that has been found to affect pharmacokinetic properties of certain therapeutic antibodies (Goetze, et al., (2011) Glycobiology 21, 949-59; Yu, et al., (2012) *MAbs* 4, 475-87). Therefore, methods for controlling the high mannose glycoform content of therapeutic proteins would be beneficial.

There is a need in the pharmaceutical industry to manipulate and control the high mannose glycoform content of recombinant therapeutic glycoproteins and methods for doing such would be useful. The invention provides a method for manipulating the high mannose glycoform content of recombinant glycoproteins by regulating ornithine metabolism in the host cells.

SUMMARY OF THE INVENTION

The invention provides a method for manipulating the high mannose glycoform content of a recombinant protein comprising culturing a host cell expressing the recombinant protein in a cell culture under conditions that regulate ornithine metabolism in the host cell.

In one embodiment ornithine metabolism in the host cell is regulated by decreasing the accumulation of ornithine in the host cell. In a related embodiment ornithine accumulation in the host cell is regulated by culturing the host cell in a cell culture medium containing an arginase inhibitor or spermine. In another related embodiment ornithine accumulation in the host cell is regulated through the addition of an arginase inhibitor to cell culture medium. In another related embodiment the arginase inhibitor is BEC (S-(2-boronoethyl)-1-cysteine) or DL-a-Difluoromethylornithine. In another related embodiment the arginase inhibitor is BEC (S-(2-boronoethyl)-1-cysteine). In another related embodiment the arginase inhibitor is DL-a-Difluoromethylornithine. In another related embodiment the concentration of the arginase inhibitor is at least 10 µM. In another related embodiment the concentration of the arginase inhibitor is from 10 µM to 2 mM. In yet another related embodiment the concentration of the arginase inhibitor is 10 µM. In yet another related embodiment the concentration of the arginase inhibitor is 0.5 mM. In yet another related embodiment the concentration of the arginase inhibitor is 1 mM. In yet another related embodiment the concentration of the arginase inhibitor is 2 mM.

In another embodiment ornithine accumulation in the host cell is regulated by adding 35 µM or less of spermine to the cell culture medium. In a related embodiment the concentration of spermine is 7 µM to 35 µM. In another related embodiment the concentration of spermine is 17 µM to 35 µM. In another related embodiment the concentration of spermine is 7 µM to 17 µM. In another related embodiment the concentration of spermine is 35 µM. In another related embodiment the concentration of spermine is 17 µM. In another related embodiment the concentration of spermine is 7 µM.

In another embodiment ornithine metabolism in the host cell is regulated by increasing the accumulation of ornithine in the host cell. In a related embodiment ornithine accumulation in the host cell is regulated by culturing the host cell in a cell culture medium containing ornithine, arginine, an ornithine decarboxylase inhibitor, an ornithine aminotransferase, a nitric oxide synthase inhibitor or an arginine decarboxylase inhibitor. In a yet another related embodiment ornithine accumulation in the host cell is regulated by the addition of at least 0.6 mM ornithine to the cell culture medium. In a yet another related embodiment the concentration of ornithine is from 0.6 to 14.8 mM. In a yet another related embodiment the concentration of ornithine is from 6 to 14.8 mM. In a yet another related embodiment the concentration of ornithine is 0.6 mM. In a yet another related embodiment the concentration of ornithine is 6 mM.

In a yet another related embodiment the concentration of ornithine is 14.8 mM. In another embodiment ornithine accumulation in the host cell is regulated by the addition of at least 8.7 mM arginine to cell culture medium. In a yet another related embodiment the concentration of arginine is from 8.7 mM to 17.5 mM. In a yet another related embodiment the concentration of arginine is 8.7 mM. In a yet another related embodiment the concentration of arginine is 17.5 mM.

In another embodiment ornithine accumulation in the host cell is regulated through the addition of an ornithine decarboxylase inhibitor, a nitric oxide synthase inhibitor, an ornithine aminotransferase inhibitor, or an arginine decarboxylase inhibitor to the cell culture medium. In a related embodiment ornithine accumulation in the host cell is regulated through the addition of an ornithine decarboxylase inhibitor to the cell culture medium. In yet another related embodiment the ornithine decarboxylase inhibitor is alpha-defluoromethylornithine (DMFO). In yet another related embodiment the ornithine decarboxylase inhibitor is piperonyl butoxide (PBO).

In another related embodiment ornithine accumulation in the host cell is regulated through the addition of an ornithine aminotransferase inhibitor to the cell culture medium. In yet another related embodiment the ornithine aminotransferase inhibitor is 5-fluoromethylornithine (F-FMOrn). In yet another related embodiment the host cell is regulated through the addition of a nitric oxide synthase inhibitor to the cell culture medium. In yet another related embodiment the nitric oxide synthase inhibitor is 2-ethyl-2-thiopseudourea or N-Nitro-L-arginine and $L^G$-monomethyl-L-arginine. In yet another related embodiment the nitric oxide synthase inhibitor is N-Nitro-L-arginine and $L^G$-monomethyl-L-arginine.

In another related embodiment ornithine accumulation in the host cell is regulated through the addition of an arginine decarboxylase inhibitor to the cell culture medium. In yet another related embodiment the arginine decarboxylase inhibitor is asymmetric dimethyl-arginine (ADMA).

The invention provides a method of producing a recombinant protein wherein the high mannose glycoform content is reduced comprising culturing a host cell which expresses the recombinant protein in a cell culture wherein ornithine metabolism is regulated by reducing ornithine accumulation in the host cell. In a related embodiment ornithine accumulation in the host cell is reduced by culturing the host cell in a cell culture medium containing an arginase inhibitor or spermine.

In a related embodiment ornithine accumulation in the host cell is reduced through the addition of an arginase inhibitor to the cell culture medium. In yet another related embodiment the arginase inhibitor is BEC (S-(2-boronoethyl)-1-cysteine) or DL-a-Difluoromethylornithine. In yet another related embodiment the arginase inhibitor is BEC (S-(2-boronoethyl)-1-cysteine). In yet another related embodiment the arginase inhibitor is DL-a-Difluoromethylornithine. In yet another related embodiment the arginase inhibitor is at least 10 µM. In yet another related embodiment the arginase inhibitor is from 10 µM to 2 mM. In yet another related embodiment the arginase inhibitor is from 10 µM to 20 µM. In yet another related embodiment the arginase inhibitor is 10 µM. In yet another related embodiment the arginase inhibitor is 0.5 mM. In yet another related embodiment the arginase inhibitor is 1 mM. In yet another related embodiment the arginase inhibitor is 2 mM.

In another embodiment ornithine accumulation in the host cell is reduced by culturing the host cell in a cell culture medium containing 35 µM or less of spermine in the cell culture medium. In yet another related embodiment the concentration of spermine is 7 µM to 35 µM. In yet another related embodiment the concentration of spermine is 17 µM to 35 µM. In yet another related embodiment the concentration of spermine is 0.07 mL/L to 0.17 mL/L. In yet another related embodiment the concentration of spermine is 35 µM. In yet another related embodiment the concentration of spermine is 17 µM. In yet another related embodiment the concentration of spermine is 7 µM.

The invention provides a method of producing a recombinant protein wherein the high mannose glycoform content is increased comprising culturing a host cell which expresses the recombinant protein in a cell culture wherein ornithine metabolism is regulated by increasing ornithine accumulation in the host cell. In a related embodiment ornithine accumulation in the host cell is increased by adding ornithine, arginine, an ornithine decarboxylase inhibitor, an ornithine aminotransferase, a nitric oxide synthase inhibitor or an arginine decarboxylase inhibitor to the cell culture medium.

In another related embodiment ornithine accumulation in the host cell is increased by the culturing the host cell in a cell culture medium containing of at least 0.6 mM ornithine. In yet another related embodiment the concentration of ornithine is from 0.6 to 14.8 mM. In yet another related embodiment the concentration of ornithine is from 6 to 14.8 mM. In yet another related embodiment the concentration of ornithine is 0.6 mM. In yet another related embodiment the concentration of ornithine is 6 mM. In yet another related embodiment the concentration of ornithine is 14.8 mM.

In another related embodiment ornithine accumulation in the host cell is increased by culturing the host cell in a cell culture medium containing at least 8.7 mM arginine. In yet another related embodiment the concentration of arginine is from 8.7 mM to 17.5 mM. In yet another related embodiment the concentration of arginine is 8.7 mM. In yet another related embodiment the concentration of arginine is 17.5 mM.

In another related embodiment ornithine accumulation is increased in the host cell by culturing the host cell in a cell culture medium containing an ornithine decarboxylase inhibitor, a nitric oxide synthase inhibitor, an ornithine aminotransferase inhibitor, or an arginine decarboxylase inhibitor. In another related embodiment ornithine accumulation in the host cell-cell is increased by culturing the host cell in a cell culture medium containing an ornithine decarboxylase inhibitor. In yet another related embodiment the ornithine decarboxylase inhibitor is alpha-defluoromethylornithine (DMFO). In yet another related embodiment the ornithine decarboxylase inhibitor is piperonyl butoxide (PBO).

In another related embodiment ornithine accumulation in the host cell is increased by culturing the host cell in a cell culture medium containing an ornithine aminotransferase inhibitor. In yet another related embodiment the ornithine aminotransferase inhibitor is 5-fluoromethylornithine (F-FMOrn).

In another related embodiment ornithine accumulation in a host cell is increased by culturing the host cell in a cell culture medium containing a nitric oxide synthase inhibitor. In yet another related embodiment the nitric oxide synthase inhibitor is 2-ethyl-2-thiopseudourea or N-Nitro-L-arginine and $L^G$-monomethyl-L-arginine.

In another embodiment ornithine accumulation in the host cell is increased by culturing the host cell in a cell culture medium containing an arginine decarboxylase inhibitor. In yet another related embodiment the arginine decarboxylase inhibitor is asymmetric dimethyl-arginine (ADMA).

In another embodiment the host cell expressing the recombinant protein is cultured in a batch culture, fed-batch culture, perfusion culture, or combinations thereof. In yet another related embodiment the culture is a perfusion culture. In yet another related embodiment perfusion comprises continuous perfusion. In yet another related embodiment the rate of perfusion is constant. In yet another related embodiment the perfusion is performed at a rate of less than or equal to 1.0 working volumes per day. In yet another related embodiment the perfusion is accomplished by alternating tangential flow.

In another embodiment the host cell expressing the recombinant protein is cultured in a bioreactor. In yet another related embodiment the bioreactor has a capacity of at least 500 L. In yet another related embodiment the bioreactor has a capacity of at least 500 L to 2000 L. In yet another related embodiment the bioreactor has a capacity of at least 1000 L to 2000 L. In yet another related embodiment the bioreactor is inoculated with at least $0.5 \times 10^6$ cells/mL.

In another embodiment the host cell expressing the recombinant protein is cultured in a serum-free cell culture medium. In another related embodiment the serum-free culture medium is a perfusion cell culture medium. In yet another related embodiment the host cells are mammalian cells. In yet another related embodiment the host cells are Chinese Hamster Ovary (CHO) cells.

In another embodiment the recombinant protein is a glycoprotein. In another embodiment the recombinant protein is selected from the group consisting of a human antibody, a humanized antibody, a chimeric antibody, a recombinant fusion protein, or a cytokine.

In another embodiment the methods above further comprise a step of harvesting the recombinant protein produced by the host cell.

In another embodiment the recombinant protein produced by the host cell is purified and formulated into a pharmaceutically acceptable formulation.

In another embodiment is provides a recombinant protein produced by any of the methods above. In a related embodiment the recombinant protein is purified. In another embodiment the recombinant protein is formulated into a pharmaceutically acceptable formulation.

DETAILED DESCRIPTION OF THE INVENTION

Figure 1:
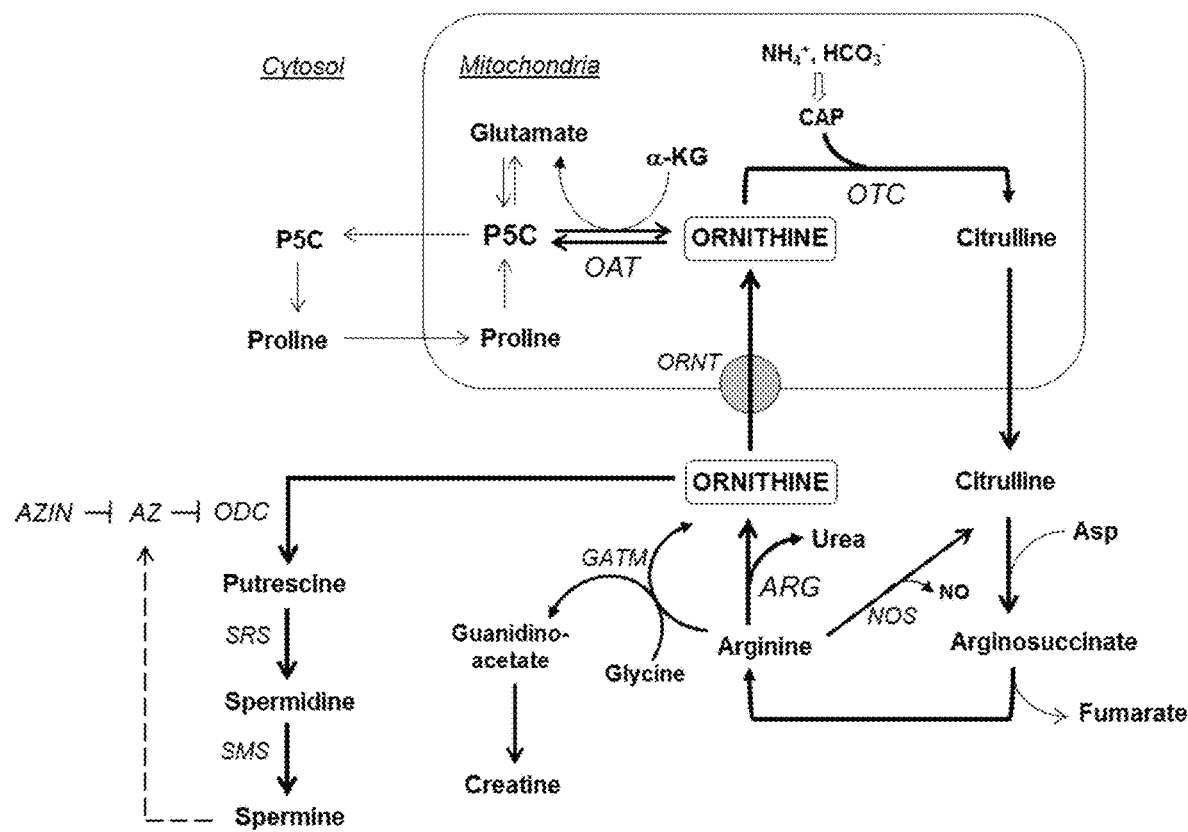
FIG. 1 Ornithine metabolism overview. ARG, Arginase; AZ, Antizyme; AZIN, Antizyme inhibitor; PSC, Pyrroline-5-carboxylate; ASP, Aspartate; ORNT, Ornithine transporter; GATM, Glycine amidinotransferase; NOS, Nitric oxide synthase; OAT, Ornithine aminotransferase; ODC, ornithine decarboxylase; OTC, ornithine transcarbamoylase; SMS, Spermine synthase; SRS, Spermidine synthase.

It was found that the high mannose glycoform content of an expressed recombinant glycoprotein was influenced by ornithine accumulation in the host cell and as a result could be manipulated by regulating ornithine metabolism in the host cell.

Ornithine is a non-protein coding amino acid involved in the urea cycle, polyamine synthesis and arginine metabolism. Ornithine is also a precursor of glutamate and proline via ornithine-δ-aminotransferase (OAT) activities, see FIG. 1. In humans, deficiency of OAT results in gyrate atrophy of the choroid and retina (GA), a disorder characterized by retinal degeneration and plasma ornithine accumulation (Takki K et al., Br J Ophthalmol. 1974; 58(11): 907-16). In a mouse model of OAT-deficiency, arginine restricted diet has shown to reduce plasma ornithine levels and prevent retinal degeneration (Wang T et al., PNAS 2000; 97(3): 1224-1229). Ornithine decarboxylase (ODC), which catalyzes the conversion of ornithine to putrescine, is the rate limiting enzyme of the polyamine biosynthetic pathway (Pegg A, JBC. 2006; 281(21): 14529-14532). ODC synthesis and stability, as well as polyamine transporter activity, is affected by environmental osmotic conditions (Munro G et al., BBA 1975; 411(2): 263-281; Tohyama et al., Eur J Biochem. 1991; 202(3):1327-1331; Michell J et al., 1998; 329:453-459). Increased polyamine biosynthesis has been associated with increased resistance to osmotic stress in plants (Alcazar R et al., Biotechnol Lett 2006; 28:1867-1876). Conversion of ornithine to citrulline is catalyzed by ornithine transcarbamylase (OTC) as part of urea cycle. OTC deficiency in humans causes accumulation of ammonia in the blood (Hopkins et al., Arch. Dis. Childh., 1969 44:143-148). Ornithine metabolism occurs in both cytosol and mitochondria, with OTC and OAT catalyzed metabolic steps taking place in the mitochondria. Mitochondrial ornithine transporter ORNT1 is required for the import of ornithine into the mitochondria. In humans, mutations in ORNT1 are responsible for hyperornithinemia-hyperammonemia-homocitrullinuria (HHH) syndrome which is characterized by elevated plasma levels of ornithine and ammonia (Camacho et al., Nat Genet (1999); 22:151-158); (Valle D et al, 2001, 1857-1896).

As described herein, the degree of ornithine accumulation in the host cell, as measured by extracellular levels of ornithine in cell culture medium, was found to correlate with high mannose glycoform content of expressed recombinant glycoproteins. Manipulating the high mannose content could be accomplished by regulating ornithine metabolism in the host cell. The invention provides a method for manipulating the high mannose glycoform content of a recombinant protein comprising culturing a host cell expressing the recombinant protein in a cell culture under conditions that regulate ornithine metabolism in the host cell. Ornithine metabolism can be regulated by decreasing or increasing accumulation of ornithine in the host cell. Methods are provided herein for producing recombinant proteins wherein the high mannose glycoform content is reduced or increased comprising culturing a host cell which expresses the recombinant protein in a cell culture wherein ornithine accumulation in the host cell is regulated.

Ornithine metabolism refers to chemical or enzymatic reactions and pathways involved in the ornithine biosynthesis, transport, catabolic process and metabolic conversions. The urea cycle, polyamine synthesis, creatine synthesis, and the mitochondrial ornithine catabolism pathways are the examples of ornithine metabolism. An overview is provided in FIG. 1.

Ornithine accumulation in a host cell is the consequence of altered ornithine metabolism. The extent of ornithine accumulation in the host cell can be modulated by regulating ornithine metabolism. Intracellular metabolite levels can be reflected in extracellular levels (i.e., detected in the cell culture medium). An indicator of the accumulation of ornithine accumulation in a host cell can be made by measuring the amount of ornithine secreted into the cell culture medium. As described herein, time-course dependent increases in ornithine levels were found in cell culture media lacking exogenous ornithine.

"High mannose glycoform content", "high mannose glycan level" and "levels of high mannose species" are used interchangeably and designated by the abbreviations "HM", "% HM", "HMN" or "% HMN" and refer to the relative percentage of mannose 5 (Man5), mannose 6 (Man6), mannose 7 (Man7), mannose 8 (Man8) and mannose 9 (Man9) glycan species combined.

It was found that the level of ornithine secreted into cell culture medium correlated with high mannose glycoform content of the recombinant glycoproteins expressed by host cells in the cell culture. When the accumulation of ornithine in a host cell was decreased by culturing the host cell in a cell culture medium containing an arginase inhibitor or spermine, the high mannose glycoform content of the expressed glycoproteins was decreased. When ornithine accumulation in the host cell was increased by culturing the host cell in a cell culture medium containing ornithine or arginine, the high mannose glycoform content of the expressed glycoproteins was increased.

The invention provides a method for regulating ornithine accumulation in a host cell by culturing the host cell in a cell culture medium containing an arginase inhibitor. Arginine is the metabolic precursor of ornithine and arginase is an enzyme which catalyzes the conversion of arginine into ornithine. It was observed that arginase mRNA expression levels correlated with the amount of ornithine accumulation when the metabolic and expression profiles of different cell lines were compared. Blocking the activity of arginase with an arginase inhibitor could potentially reduce ornithine production levels. However, the effectiveness of arginase inhibitors may be compromised due to the high level of arginine in cell culture medium. In addition, there are other metabolic precursors of ornithine (i.e. glutamate and proline, see FIG. 1) that may contribute to ornithine accumulation.

As described herein, it was found that high mannose glycoform content of a recombinant protein expressed by the cultured host cell could be modulated by adding an arginase inhibitor to the cell culture medium. Blocking the activity of arginase reduced the amount of ornithine production in the host cells, lowered the high mannose glycan level of the expressed recombinant glycoproteins.

Arginase also inhibits ornithine transcarbamoylase (OTC) (Vissers et al., (1982) J. Gen. Microbio. 128:1235-1247). Blocking the activity of arginase not only reduces ornithine production from arginine but could potentially relieve the repression of OTC activity, allowing ornithine conversion to citrulline, allowing for additional reduction of ornithine accumulation (see FIG. 1).

In patients with OTC deficiency, ammonia levels are increased. If enhanced arginase expression or activity in host cell lines expressing recombinant proteins with high levels of high mannose glycans induces OTC inhibition, this m also result in ammonia level increase. Increase in the intracellular levels of ammonia could potentially alter pH gradient in Golgi apparatus and induce suboptimal relocalization of glycosyltransferases, resulting in higher levels of high mannose glycans due to incomplete glycan branching in Golgi complex (Campbell et al, (1973) NJM 288 (1):1-6; Hopkins et al., (1969) Archive of Disease in Childhood 44(234):143-148; Willing et al, (2001) Amino Acids 21(3): 303-318; Park et al., (2000) J. Biotechnol 81(2):129-140; Rivinoja et al., (2009) J. Cell Physiol. 220(1):144-154; and Axelsson et al., (2001) Glycobiology 11(8): 633-644).

Useful arginase inhibitors are known in the art and available from commercial sources. Such arginase inhibitors include, BEC Hydrochloride; DL-α, Diflouromethylornithine Hydrochloride; $N^G$-Hydroxy-L-arginine and Nω-Hydroxy-nor-arginine. In one embodiment the arginase inhibitor is BEC (S-(2-boronoethyl)-1-cysteine) or DL-a-Difluoromethylornithine. In one embodiment of the invention the arginase inhibitor is BEC (S-(2-boronoethyl)-1-cysteine). In one embodiment of the invention the arginase inhibitor is DL-a-Difluoromethylornithine.

Arginase inhibitors can be added to cell culture medium at concentrations of at least 10 μM to decrease high mannose glycan levels of expressed recombinant proteins without significantly affecting productivity. In one embodiment, the concentration of the arginase inhibitor is from 10 μM to 2 mM. In another embodiment, the concentration of the arginase inhibitor is 10 µM. In another embodiment the concentration of the arginase inhibitor is 0.5 mM. In another embodiment the concentration of the arginase inhibitor is 1 mM. In another embodiment the concentration of the arginase inhibitor is 2 mM.

Ornithine accumulation in the host cell can also be regulated by culturing the host cell in a cell culture medium containing spermine, as described in the Examples below. Ornithine, via the action of ornithine decarboxylase (ODC), is the starting point for the polyamine pathway and synthesis of the polyamines putrescine, spermidine and spermine. Exogenously added spermine can be used to inactivate ODC directly, or through antizyme, see FIG. 1. Inactivation of ODC can lead to accumulation of ornithine as described below. By limiting the amount of exogenously added spermine, suppression of ODC activity can be relieved and ornithine can be metabolized through the polyamine pathway, thereby reducing the overall ornithine accumulation in the host cell.

Spermine can be added to cell culture medium at concentrations of less than or equal to 35 µM to decrease high mannose glycan levels of expressed recombinant proteins without significantly affecting productivity. In one embodiment the concentration of spermine is 7 µM to 35 µM. In one embodiment the concentration of spermine is 17 µM to 35 µM. In one embodiment the concentration of spermine is 7 µM to 17 µM. In another embodiment the concentration of spermine is 35 µM. In another embodiment the concentration of spermine is 17 µM. In another embodiment the concentration of spermine is 7 µM.

Another method for regulating ornithine metabolism is to increase the accumulation of ornithine. In one embodiment the invention provides regulating ornithine accumulation in a host cell by culturing the host cell in a cell culture medium containing ornithine, arginine, an ornithine decarboxylase inhibitor, an ornithine aminotransferase, a nitric oxide synthase inhibitor or an arginine decarboxylase inhibitor.

As described herein, levels of extracellular ornithine in conditioned cell culture media was found to correlate to high mannose glycan levels on recombinant glycoproteins. It was found that culturing host cells expressing recombinant proteins in a cell culture medium containing ornithine resulted in recombinant glycoproteins having increased levels of high mannose glycans.

As described above, ornithine accumulation in cell culture media likely reflects alterations in ornithine metabolism which can lead to accumulation of ammonia, similar to patients carrying defective genes of ornithine metabolism (eg. OTC deficiency or ORNT1 mutation). While the cellular mechanism behind ammonia induced high mannose increase is not known, it has been suggested that alteration in the pH gradient in Golgi can lead to suboptimal relocalization of glycosyltransferases. These changes could lead to decreased availability of glycosylation enzymes to complete glycan branching, and thus result in higher levels of high mannose glycan levels.

Another possibility is that ornithine accumulation potentially induces disturbance of redox homeostasis (Zanatta et al., (2013) Life sciences 93(4): 161-168). Ornithine correlates positively with high mannose suggesting the possibility that high mannose glycoform content is regulated by cellular redox state. Ornithine can increase the levels of lipid oxidation. Since many of the glycosylation regulating enzymes are lipid membrane bound, alterations in lipid oxidation caused by ornithine accumulation could potentially alter the integrity and activity of glycosylation regulating enzymes in Golgi and ER, and subsequently affect high mannose glycoform contents.

Ornithine can be added to cell culture medium at concentrations of at least 0.6 mM, to increase high mannose glycan levels of expressed recombinant proteins without significantly affecting productivity. In one embodiment the concentration of ornithine is from 0.6 mM to 14.8 mM. In one embodiment the concentration of ornithine is from 6 mM to 14.8 mM. In another embodiment the concentration of ornithine is 0.6 mM. In another embodiment the concentration of ornithine is 6 mM. In another embodiment the concentration of ornithine is 14.8 mM.

Arginine is the metabolic precursor of ornithine. It was found that high mannose glycan levels were increased in recombinant proteins expressed in host cells cultivated in cell culture medium containing exogenous arginine. Increasing the amount of exogenous arginine increased the amount of metabolic precursor available for ornithine synthesis, thereby increasing the levels of ornithine in host cells.

The invention provides regulating ornithine accumulation in host cells by adding arginine at concentrations of at least 8.7 mM to increase high mannose glycan levels of expressed recombinant proteins without significantly affecting productivity. In one embodiment the concentration of arginine is from 8.7 to 17.5 mM. In another embodiment the concentration of arginine is 8.7 mM. In another embodiment the concentration of arginine is 17.5 mM.

Ornithine accumulation may be regulated through the addition to cell culture medium of inhibitors of Ornithine decarboxylase (ODC), Ornithine aminotransferase (OAT), Nitric oxide synthase (NOS) or Arginine Decarboxylase (ADC), thereby providing a way to regulate ornithine metabolism and accumulation of ornithine in the host cell to manipulate the high mannose glycoform content of a recombinant protein.

Ornithine accumulation can be increased by blocking the activity of ornithine metabolizing enzymes such as ODC and OAT (see FIG. 1). Small-molecule inhibitors specific for ODC such as alpha-difluoromethylornithine (DFMO) and piperonyl butoxide (PBO) are commercially available. OAT is blocked by 5-fluoromethylornithine (5-FMOrn) T (Daune et al., 1988, Biochem J. 253:481-488). The invention provides supplementing a cell culture with these inhibitors to increase ornithine accumulation in the host cells to manipulate the high mannose glycoform content of a recombinant protein.

Ornithine accumulation may be regulated by blocking the activity of the enzymes that regulate arginine accumulation (FIG. 1). Inhibiting the activity of nitric oxide synthase by small molecule inhibitors such as 2-ethyl-2-thiopseudourea and N-Nitro-L-arginine and $L^G$-monomethyl-L-arginine and/or arginine decarboxylase activity by asymmetric dimethyl-arginine (ADMA) may enhance flux of ornithine conversion from arginine. The invention provides supplementing a cell culture with these inhibitors to increase in ornithine accumulation in the host cell to manipulate the high mannose glycoform content of a recombinant protein.

In one embodiment of the invention is provided that the cell culture medium is a serum-free cell culture medium. In one embodiment the cell culture medium is a perfusion cell culture medium.

As used herein, the terms "cell culturing medium" (also called "culture medium," "cell culture media," "tissue culture media,") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

The nutrient solution may optionally be supplemented with additional components to optimize growth of cells, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal protein (peptone or peptone mixtures, which can be obtained from animal byproducts, purified gelatin or plant material); antibiotics, e.g., gentamycin; ell protectants or surfactants, e.g., Pluronic® F68; polyamines, e.g., putrescine, spermidine or spermine (see e.g., WIPO Publication No. WO 2008/154014) and pyruvate (see e.g. U.S. Pat. No. 8,053,238) depending on the requirements of the cells to be cultured and/or the desired cell culture parameters.

Cell culture medium include those that are typically employed in and/or are known for use with any cell culture process, such as, but not limited to, batch, extended batch, fed-batch and/or perfusion or continuous culturing of cells.

Cell culture medium components may be completely milled into a powder medium formulation; partially milled with liquid supplements added to the cell culture medium as needed; or nutrients may be added in a completely liquid form to the cell culture.

A "base" (or batch) cell culture medium refers to a cell culture medium that is typically used to initiate a cell culture and is sufficiently complete to support the cell culture.

A "growth" cell culture medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium refers to a cell culture medium that is typically used in cell cultures during the transition and production phases when exponential growth is ending and protein production takes over, and is sufficiently complete to maintain a desired cell density, viability and/or product titer these phases.

A "perfusion" cell culture medium refers to a cell culture medium that is typically used in cell cultures that are maintained by perfusion or continuous culture methods and is sufficiently complete to support the cell culture during this process. Perfusion cell culture medium formulations may be enriched or more concentrated than base cell culture medium formulations to accommodate for the method used to remove the spent medium. Perfusion cell culture medium can be used during both the growth and production phases.

Concentrated cell culture medium can contain some or all of the nutrients necessary to maintain the cell culture; in particular, concentrated medium can contain nutrients identified as or known to be consumed during the course of the production phase of the cell culture. Concentrated medium may be based on just about any cell culture media formulation. Such a concentrated feed medium can contain some or all the components of the cell culture medium at, for example, about 2×, 3×, 4×, 5×, 6×, 7×, 8×, 9×, 10×, 12×, 14×, 16×, 20×, 30×, 50×, 100×, 200×, 400×, 600×, 800×, or even about 1000× of their normal amount.

Cell cultures can also be supplemented with independent concentrated feeds of particular nutrients which may be difficult to formulate or are quickly depleted in cell cultures. Such nutrients may be amino acids such as tyrosine, cysteine and/or cystine (see e.g., WIPO Publication No. 2012/145682). In one embodiment, a concentrated solution of tyrosine is independently fed to a cell culture grown in a cell culture medium containing tyrosine, such that the concentration of tyrosine in the cell culture does not exceed 8 mM. In another embodiment, a concentrated solution of tyrosine and cystine is independently fed to the cell culture being grown in a cell culture medium lacking tyrosine, cystine or cysteine. The independent feeds can begin prior to or at the start of the production phase. The independent feeds can be accomplished by fed batch to the cell culture medium on the same or different days as the concentrated feed medium. The independent feeds can also be perfused on the same or different days as the perfused medium.

Cell culture medium, in certain embodiments, is serum-free and/or free of products or ingredients of animal origin. Cell culture medium, in certain embodiments, is chemically defined, where all of the chemical components are known.

As is appreciated by the practitioner, animal or mammalian cells are cultured in a medium suitable for the particular cells being cultured and which can be determined by the person of skill in the art without undue experimentation. Commercially available media can be utilized and include, but is not limited to, Iscove's Modified Dulbecco's Medium, RPMI 1640, Minimal Essential Medium-alpha. (MEM-alpha), Dulbecco's Modification of Eagle's Medium (DMEM), DME/F12, alpha MEM, Basal Medium Eagle with Earle's BSS, DMEM high Glucose, with Glutamine, DMEM high glucose, without Glutamine, DMEM low Glucose, without Glutamine, DMEM:F12 1:1, with Glutamine, GMEM (Glasgow's MEM), GMEM with glutamine, Grace's Complete Insect Medium, Grace's Insect Medium, without FBS, Ham's F-10, with Glutamine, Ham's F-12, with Glutamine, IMDM with HEPES and Glutamine, IMDM with HEPES and without Glutamine, IP41 Insect Medium, 15 (Leibovitz)(2×), without Glutamine or Phenol Red, 15 (Leibovitz), without Glutamine, McCoy's 5A Modified Medium, Medium 199, MEM Eagle, without Glutamine or Phenol Red (2×), MEM Eagle-Earle's BSS, with glutamine, MEM Eagle-Earle's BSS, without Glutamine, MEM Eagle-Hanks BSS, without Glutamine, NCTC-109, with Glutamine, Richter's CM Medium, with Glutamine, RPMI 1640 with HEPES, Glutamine and/or Penicillin-Streptomycin, RPMI 1640, with Glutamine, RPMI 1640, without Glutamine, Schneider's Insect Medium or any other media known to one skilled in the art, which are formulated for particular cell types. To the foregoing exemplary media can be added supplementary components or ingredients, including optional components, in appropriate concentrations or amounts, as necessary or desired, and as would be known and practiced by those having in the art using routine skill.

In one embodiment of the invention is provided that the host cells are mammalian cells. In one embodiment the host cells are Chinese Hamster Ovary (CHO) cells.

Cell lines (also referred to as "host cells") used in the invention are genetically engineered to express a polypeptide of commercial or scientific interest. Cell lines are typically derived from a lineage arising from a primary culture that can be maintained in culture for an unlimited time. The cells can contain introduced, e.g., via transformation, transfection, infection, or injection, expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in J. Sambrook et al., 2012, *Molecular Cloning, A Laboratory Manual*, 4$^{th}$ edition Cold Spring Harbor Press, Plainview, N.Y. or any of the previous editions; F. M. Ausubel et al., 2013, *Current Protocols in Molecular Biology*, John Wiley & Sons, New York, N.Y., or any of the previous editions; Kaufman, R. J., *Large Scale Mammalian Cell Culture*, 1990, all of which are incorporated herein for any purpose.

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or other factors, such as those described herein. The cells are typically selected that can express and secrete proteins, or that can be molecularly engineered to express and secrete, large quantities of a particular protein, more particularly, a glycoprotein of interest, into the culture medium. It will be understood that the protein produced by a host cell can be endogenous or homologous to the host cell. Alternatively, the protein is heterologous, i.e., foreign, to the host cell, for example, a human protein produced and secreted by a Chinese hamster ovary (CHO) host cell. Additionally, mammalian proteins, i.e., those originally obtained or derived from a mammalian organism, are attained by the methods the present invention and can be secreted by the cells into the culture medium.

The methods of the present invention can be used in the culture of a variety of cells. In one embodiment, the cultured cells are eukaryotic cells such as plant and/or animal cells. The cells can be mammalian cells, fish cells, insect cells, amphibian cells or avian cells. A wide variety of mammalian cell lines suitable for growth in culture are available from the American Type Culture Collection (Manassas, Va.) and other depositories as well as commercial vendors. Cell that can be used in the processes of the invention include, but not limited to, MK2.7 cells, PER-C6 cells, Chinese hamster ovary cells (CHO), such as CHO-K1 (ATCC CCL-61), DG44 (Chasin et al., 1986, *Som. Cell Molec. Genet.*, 12:555-556; Kolkekar et al., 1997, *Biochemistry*, 36:10901-10909; and WO 01/92337 A2), dihydrofolate reductase negative CHO cells (CHO/−DHFR, Urlaub and Chasin, 1980, *Proc. Natl. Acad. Sci. USA*, 77:4216), and dp12.CHO cells (U.S. Pat. No. 5,721,121); monkey kidney cells (CV1, ATCC CCL-70); monkey kidney CV1 cells transformed by SV40 (COS cells, COS-7, ATCC CRL-1651); HEK 293 cells, and Sp2/0 cells, 5L8 hybridoma cells, Daudi cells, EL4 cells, HeLa cells, HL-60 cells, K562 cells, Jurkat cells, THP-1 cells, Sp2/0 cells, primary epithelial cells (e.g., keratinocytes, cervical epithelial cells, bronchial epithelial cells, tracheal epithelial cells, kidney epithelial cells and retinal epithelial cells) and established cell lines and their strains (e.g., human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.*, 383:44-68); MCR 5 cells; FS4 cells; PER-C6 retinal cells, MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GEL cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CV-1 cells, COS-1 cells, COS-3 cells, COS-7 cells, African green monkey kidney cells (VERO-76, ATCC CRL-1587; VERO, ATCC CCL-81); DBS-FrhL-2 cells, BALB/3T3 cells, F9 cells, SV-T2 cells, M-MSV-BALB/3T3 cells, K-BALB cells, BLO-11 cells, NOR-10 cells, C$_3$H/IOTI/2 cells, HSDM$_1$C$_3$ cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntac cells, SIRC cells, C$_{II}$ cells, and Jensen cells, or derivatives thereof) or any other cell type known to one skilled in the art.

Cells may be suitable for adherent, monolayer or suspension culture, transfection, and expression of proteins, for example, antibodies. The cells can be used with batch, fed batch and perfusion or continuous culture methods.

In one embodiment of the invention the host cell expressing the recombinant protein is cultured in a bioreactor. In another embodiment of the invention the bioreactor has a capacity of at least 500 L. In a related embodiment the bioreactor has a capacity of at least 500 L to 2000 L. In yet another related embodiment the bioreactor has a capacity of at least 1000 L to 2000 L. In one embodiment of the invention the cell culture is established by inoculating the bioreactor with at least 0.5×10$^6$ cells/mL in a serum-free culture medium. In one embodiment, the invention further comprising a step of harvesting the recombinant protein produced by the host cell. In one embodiment the invention provides that the recombinant protein produced by the host cell is purified and formulated into a pharmaceutically acceptable formulation.

For the purposes of understanding, yet without limitation, it will be appreciated by the skilled practitioner that cell cultures and culturing runs for protein production can include three general types; namely, batch culture, extended batch, fed-batch culture, perfusion culture, or combinations thereof. In batch culture, cells are initially cultured in medium and this medium is not removed, replaced, or supplemented, i.e., the cells are not "fed" with fresh medium, during or before the end of the culturing run. The desired product is harvested at the end of the culturing run.

For fed-batch cultures, the culturing run time is increased by supplementing the culture medium one or more times daily (or continuously) with fresh medium during the run, i.e., the cells are "fed" with new medium ("fed medium") during the culturing period. Fed-batch cultures can include the various feeding regimens and times as described above, for example, daily, every other day, every two days, etc., more than once per day, or less than once per day, and so on. Further, fed-batch cultures can be fed continuously with feeding medium. The desired product is then harvested at the end of the culturing/production run.

Perfusion culture is one in which the cell culture receives fresh perfusion medium and spent medium is removed. Perfusion of fresh media into the cell culture and removal of spend media can be continuous, step-wise, intermittent, or a combination of any or all of these. Perfusion rates can range from less than one working volume per day to many working volumes per day. Preferably the cells are retained in the culture and the spent medium that is removed is substantially free of cells or has significantly fewer cells than the culture. Recombinant proteins expressed by the cell culture can also be retained in the culture or removed with the spent medium. Removal of the spent medium may be accomplished by a number of means including centrifugation, sedimentation, or filtration, See e.g. Voisard et al., (2003), Biotechnology and Bioengineering 82:751-65. A preferred filtration method is alternating tangential flow filtration. The alternating tangential flow is maintained by pumping medium through hollow-fiber filter modules using an ATF device. See e.g. U.S. Pat. No. 6,544,424; Furey (2002) Gen. Eng. News. 22 (7), 62-63. The filters separate particles on basis of size or molecular weight. Depending on the application, filters may be chosen based on pore size or a molecular weight cut off (MWCO) value. Filters include membrane filters, ceramic filters and metal filters and may be in any shape, including spiral wound or tubular or in the form of a sheet.

The term "perfusion flow rate" is the amount of media that is passed through (added and removed) from a bioreactor, typically expressed as some portion of or a multiple of the working volume, in a given time. "Working volume" refers to the amount of bioreactor volume used for cell culture. In one embodiment the perfusion flow rate is one working volume or less per day.

Cell culture can be carried out under conditions for small to large scale production of recombinant proteins using culture vessels and/or culture apparatuses that are conventionally employed for animal or mammalian cell culture. As is appreciated by those having skill in the art, tissue culture dishes, T-flasks and spinner flasks are typically used on a laboratory bench scale. For culturing on a larger scale equipment such as. but not limited to, fermentor type tank culture devices, air lift type culture devices, fluidized bed bioreactors, hollow fiber bioreactors, roller bottle cultures, stirred tank bioreactor systems, packed bed type culture devices, and single use disposable bags or any other suitable devise known to one skilled in the art can be used. Microcarriers may or may not be used with the roller bottle or stirred tank bioreactor systems. The systems can be operated in a batch, fed-batch or perfusion/continuous mode. In addition, the culture apparatus or system may be equipped with additional apparatus, such a cell separators using filters, gravity, centrifugal force, and the like.

The production of recombinant proteins can be done in multiple phase culture processes. In a multiple phase process, cells are cultured in two or more distinct phases. For example cells may be cultured first in one or more growth phases, under environmental conditions that maximize cell proliferation and viability, then transitioned to a production phase, under conditions that maximize protein production. In a commercial process for production of recombinant proteins by mammalian cells, there are commonly multiple, for example, at least about 2, 3, 4, 5, 6, 7, 8, 9, 10 or more growth phases that occur in different culture vessels (N-x to N-1) preceding a final production culture. The growth and production phases may be preceded by, or separated by, one or more transition phases. A production phase can be conducted at large scale.

The term "growth phase" of a cell culture refers to the period of exponential cell growth (i.e., the log phase) where the cells are generally rapidly dividing. Cells are maintained at the growth phase for a period of about one day, or about two days, or about three days, or about four days, or longer than four days. The duration of time for which the cells are maintained at growth phase will vary based on the cell-type and rate of growth of cells and the culture conditions, for example.

The term "transition phase" refers to a period of time between the growth phase and the production phase. Generally, transition phase is the time during which culture conditions may be controlled to support a shift from growth phase to production phase. Various cell culture parameters which may be controlled include but are not limited to, one or more of, temperature, osmolality, vitamins, amino acids, sugars, peptones, ammonium and salts.

The term "production phase" of a cell culture refers to the period of time where the cell growth has plateaued. The logarithmic cell growth typically ends before or during this phase and protein production takes over. Fed batch and perfusion cell culture processes supplement the cell culture medium or provide fresh medium so as to achieve and maintain desired cell density, viability and product titer at this stage. A production phase can be conducted at large scale. Large scale cell cultures can be maintained in a volume of at least about 100, 500, 1000, 2000, 3000, 5000, 7000, 8000, 10,000, 15,000, 20,000 liters. In a preferred embodiment the production phase is conducted in 500 L, 1000 L and/or 2000 L bioreactors.

Typically the cell cultures that precede a final production culture go through two prior phases, seed and inoculum trains. The seed train phase (N-X) takes place at small scale where cells are quickly expanded in number. At the inoculums train phase (N-1), cells are further expanded to generate the inoculum for the production bioreactor, such as an inoculums of at least $0.5 \times 10^6$ cells/mL. Seed and N-1 trains can be produced by any culture method, typically batch cell cultures. N-1 cell densities of $>15 \times 10^6$ cells/mL are typical for seeding production bioreactors. Higher N-1 cell densities can decrease or even eliminate the time needed to reach a desired cell density in the production bioreactor. A preferred method for achieving higher N-1 cell densities is perfusion culture using alternating tangential flow filtration. An N-1 cell culture grown by means of a perfusion process using alternating tangential flow filtration can provide cells at any desired density, such as densities of >90×10$^6$ cells/mL or more. The N-1 cell culture can be used to generate a single bolus inoculation culture or can be used as a rolling seed stock culture that is maintained to inoculate multiple production bioreactors. The inoculation density can have a positive impact on the level of recombinant protein produced. Product levels tend to increase with increasing inoculation density. Improvement in titer is tied not only to higher inoculation density, but is likely to be influenced by the metabolic and cell cycle state of the cells that are placed into production.

The term "cell density" refers to the number of cells in a given volume of culture medium. "Viable cell density" refers to the number of live cells in a given volume of culture medium, as determined by standard viability assays (such as trypan blue dye exclusion method). The term "packed cell volume" (PCV), also referred to as "percent packed cell volume" (% PCV), is the ratio of the volume occupied by the cells, to the total volume of cell culture, expressed as a percentage (see Stettler, et al., (2006) Biotechnol Bioeng. December 20: 95(6):1228-33). Packed cell volume is a function of cell density and cell diameter; increases in packed cell volume could arise from increases in either cell density or cell diameter or both. Packed cell volume is a measure of the solid level in the cell culture.

During production, a growth phase may occur at a higher temperature than a production phase. For example, a growth phase may occur at a first temperature set-point from about 35° C. to about 38° C., and a production phase may occur at a second temperature set-point from about 29° C. to about 37° C., optionally from about 30° C. to about 36° C. or from about 30° C. to about 34° C.

In addition, chemical inducers of protein production, such as caffeine, butyrate, and/or hexamethylene bisacetamide (HMBA), may be added at the same time as, before, or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Another method to maintain cells at a desired physiological state is to induce cell growth-arrest by exposure of the cell culture to low L-asparagine conditions (see e.g., WIPO Publication No. WO2013/006479). Cell growth-arrest may be achieved and maintained through a culture medium that contains a limiting concentration of L-asparagine and maintaining a low concentration of L-asparagine in the cell culture. Maintaining the concentration of L-asparagine at 5 mM or less can be used to maintain cells in a growth-arrested state whereby productivity increased.

Cell cycle inhibitors, compound known or suspected to regulate cell cycle progression and the associated processes of transcription, DNA repair, differentiation, senescence and apoptosis related to this are also useful to induce cell growth-arrest. Cell cycle inhibitors that interact with the cycle machinery, such as cyclin-dependent kinases (CDKs) are useful as are those molecules that interact with proteins from other pathways, such as AKT, mTOR, and other pathways that affect, directly or indirectly, the cell cycle.

Cell culture conditions suitable for the methods of the present invention are those that are typically employed and known for batch, fed-batch, or perfusion (continuous) culturing of cells or any combination of those methods, with attention paid to pH, dissolved oxygen ($O_2$), and carbon dioxide ($CO_2$), agitation and humidity, and temperature.

The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products known in the art and/or available from commercial vendors. The purified proteins can then be "formulated", meaning buffer exchanged into a pharmaceutically acceptable formulation, sterilized, bulk-packaged, and/or packaged for a final user. Pharmaceutically acceptable formulations can include diluents, carriers, solubilizers, emulsifiers, preservatives, and/or adjuvants. Preparing pharmaceutically acceptable formulations is within the skill of one in the art and includes those described in *Remington's Pharmaceutical Sciences*, 18th ed. 1995, Mack Publishing Company, Easton, Pa.

In one embodiment of the invention is provided that the recombinant protein is a glycoprotein. In one embodiment of the invention is provided that the recombinant protein is selected from the group consisting of a human antibody, a humanized antibody, a chimeric antibody, a recombinant fusion protein, or a cytokine. Also provided is a recombinant protein produced by the method of the invention. In one embodiment the recombinant protein according is formulated into a pharmaceutically acceptable formulation.

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation resulting in glycoproteins, lipid attachment, sulfation, gamma-carboxylation of glutamic acid residues, hydroxylation and ADP-ribosylation.

As used herein, the term "glycoprotein" refers to peptides and proteins, including antibodies, having at least one oligosaccharide side chain including mannose residues. Glycoproteins may be homologous to the host cell, or may be heterologous, i.e., foreign, to the host cell being utilized, such as, for example, a human glycoprotein produced by a Chinese hamster ovary (CHO) host cell. Such glycoproteins are generally referred to as "recombinant glycoproteins." In certain embodiments, glycoproteins expressed by a host cell are directly secreted into the medium.

Proteins can be of scientific or commercial interest, including protein-based drugs. Proteins include, among other things, antibodies, fusion proteins, and cytokines. Peptides, polypeptides and proteins may be produced by recombinant animal cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Nonlimiting examples of mammalian proteins that can be advantageously produced by the methods of this invention include proteins comprising amino acid sequences identical to or substantially similar to all or part of one of the following proteins: tumor necrosis factor (TNF), flt3 ligand (WO 94/28391), erythropoietin, thrombopoietin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No.

588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research*, all volumes (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook*, Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064,), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-10, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizumab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Håkansson et al. (1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc). Chimeric proteins and polypeptides, as well as fragments or portions, or mutants, variants, or analogs of any of the aforementioned proteins and polypeptides are also included among the suitable proteins, polypeptides and peptides that can be produced by the methods of the present invention.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference. What is described in an embodiment of the invention can be combined with other embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

Figure 2:
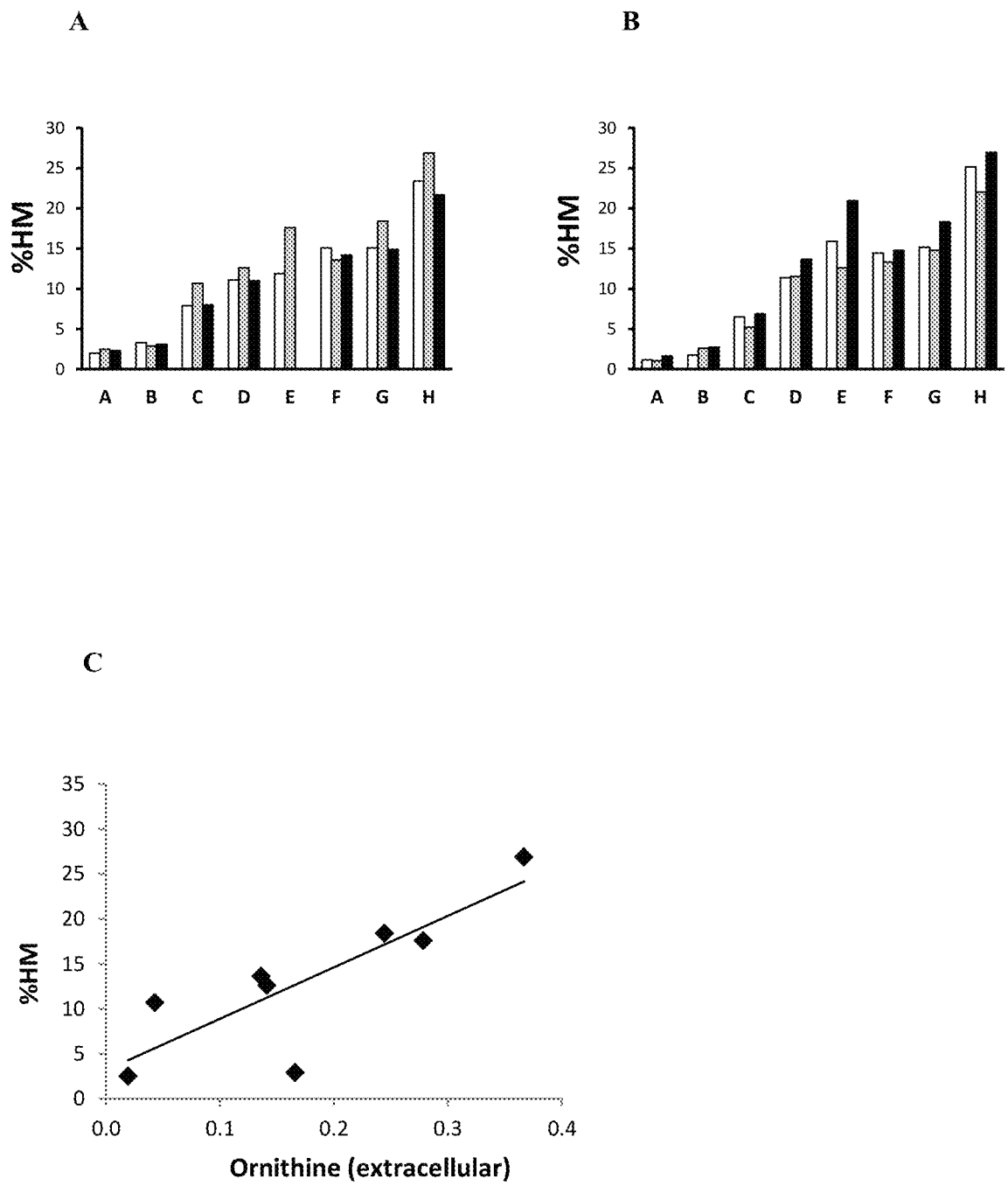
FIG. 2 Identification of ornithine as a metabolic marker associated with high mannose glycan levels. High mannose glycan levels (% HM) of the secreted recombinant monoclonal antibodies from eight different cell lines (Cell line A through H) detected on day 8 (D8, white bars), day 9 (D9, gray bars) and day 10 (D10, black bars) of the fed-batch process evaluated under Media #1 (A) or Media #2 (B). Correlation between high mannose glycan levels and extracellular ornithine levels detected in the spent media (C). The average day 9 ornithine level and high mannose glycan level from the eight cell lines were compared. Pearson's R-value, R=0.83.

Extracellular ornithine levels were found to correlate with high mannose glycoform contents. Eight CHO cell lines expressing recombinant antibodies having high mannose glycoform content ranging from <5% to >20% were chosen for this experiment (Cell line A-Cell line H). The cells were grown in a 10 day fed-batch culture in shake flasks using two different proprietary cell culture media, each containing no ornithine (Media #1 and Media #2). Spent media samples were taken on days 8, 9 and 10 of the culture and were subjected to a large-scale metabolomics analysis. % HM was determined using an Endo-H rCE-SDS method, later replaced by the HILIC method described below. Relative levels of ornithine in the spent media were determined by large-scale metabolomics analysis in which media components were separated by liquid chromatography and detected by high-resolution spectrometry. Components were identified by matching their fragmentation spectra to a library of spectra of known compounds. The relative abundance of each component was determined from the peak area of its mass spectrometry signals. The high mannose glycan levels (% HM) of the secreted monoclonal antibodies from Cell lines A-H on days 8, 9 and 10 in Media #1 and Media #2 is shown in FIGS. 2A and B. FIG. 2C shows the correlation between % high mannose and extracellular ornithine levels. The correlation was determined by comparing all 8 cell lines (represented by the squares) using data from Day 9 samples. The results suggested a strong correlation between high mannose glycoform contents and extracellular levels of ornithine.

Next, Cell line H was grown in fed batch culture in a 3 L bioreactor. Culture duration was 12 days. Four bolus feeds of 7%, 9%, 9% and 9% were made on days 3, 5, 7 and 9. In addition, 50% glucose solution was added daily starting on day 3 as required to maintain a glucose concentration above 2 g/L. Production bioreactors were inoculated at 15×10$^5$ cells/ml after 4 days of growth. The cells were maintained in growth medium until a production phase was initiated. Eight different process conditions were then compared. Condition #1 acted as the control. No alterations were made to the production feed media.

In Condition #2, betaine was supplemented in the production feed media at a concentration of 24 mM on day 0. No further betaine supplements were provided. Four bolus feeds of 7%, 9%, 9% and 9% were made on days 3, 5, 7 and 9. In addition, 50% glucose solution was added daily starting on day 3 as required to maintain a glucose concentration above 2 g/L.

In Conditions #3 and #4, removal of copper sulfate was tested. Copper sulfate was removed from the production base media powder. Condition #3 served as a control, a copper sulfate stock solution was added to the base media. In Condition #4, no copper sulfate was added to any media, creating a copper-deficient culture environment. For both Condition #3 and #4, both were treated with the same bolus "feed" media which contains copper.

In Conditions #5-#8, high and low osmolality was tested. In Conditions #5 and #6, the cells were fed with 90% production batch medium, i.e., 10% less nutrients were provided, which translates to the cells experiencing reduced osmolality. In Condition #6, the cell culture media was brought back to the control level, ~300 mOsm, by titration with NaCl. In Condition #7 and #8 the cells were fed with 85% feed medium, with the medium in Condition #8 being brought back to the control level by titration with NaCl.

Spent media samples were taken on days 3, 6, 8, 9 and 10 of the culture and were subjected to a large-scale metabolomics analysis.

Again, there was a significant correlation between extracellular ornithine and high mannose glycoform contents.

Figure 3:
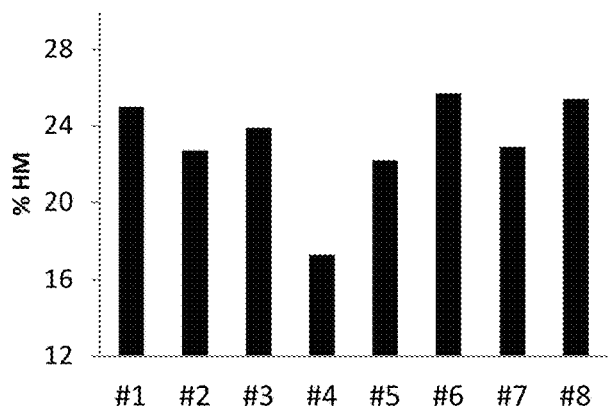
FIG. 3 Correlation between high mannose and extracellular ornithine levels: A) High mannose glycoform content detected when cell line H was exposed to eight different production conditions (#1 thru #8). B) Corresponding extracellular relative ornithine levels. C) Correlation between % high mannose glycoform content and extracellular relative ornithine levels. Pearson's R-value, R=0.78.
Figure 3:
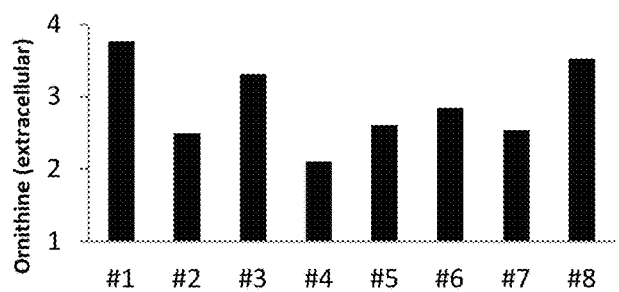
Figure 3:
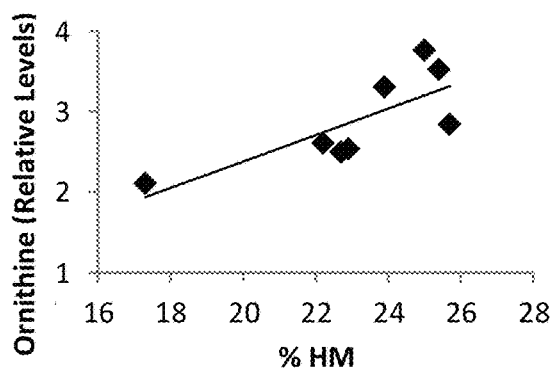

FIG. 3A shows the percent high mannose glycan levels detected when Cell line H was exposed to the 8 different bioreactor conditions (#1 thru #8). FIG. 3B shows the corresponding extracellular ornithine levels. FIG. 3C shows the correlation between % high mannose and extracellular ornithine levels. The correlation was determined by comparing all 8 conditions (represented by the squares) using data from Day 9 samples.

Example 2

The mRNA expression levels of Arginase 1 were measured on selected days during a 10-day fed-batch production culture using the eight cell lines described in Example 1.

The mRNA expression levels were assessed using a QuantiGene Multiplex Assay kit, (Affymetrix, Inc., Santa Clara, Calif.) according to the manufacturer's instructions.

Figure 4:
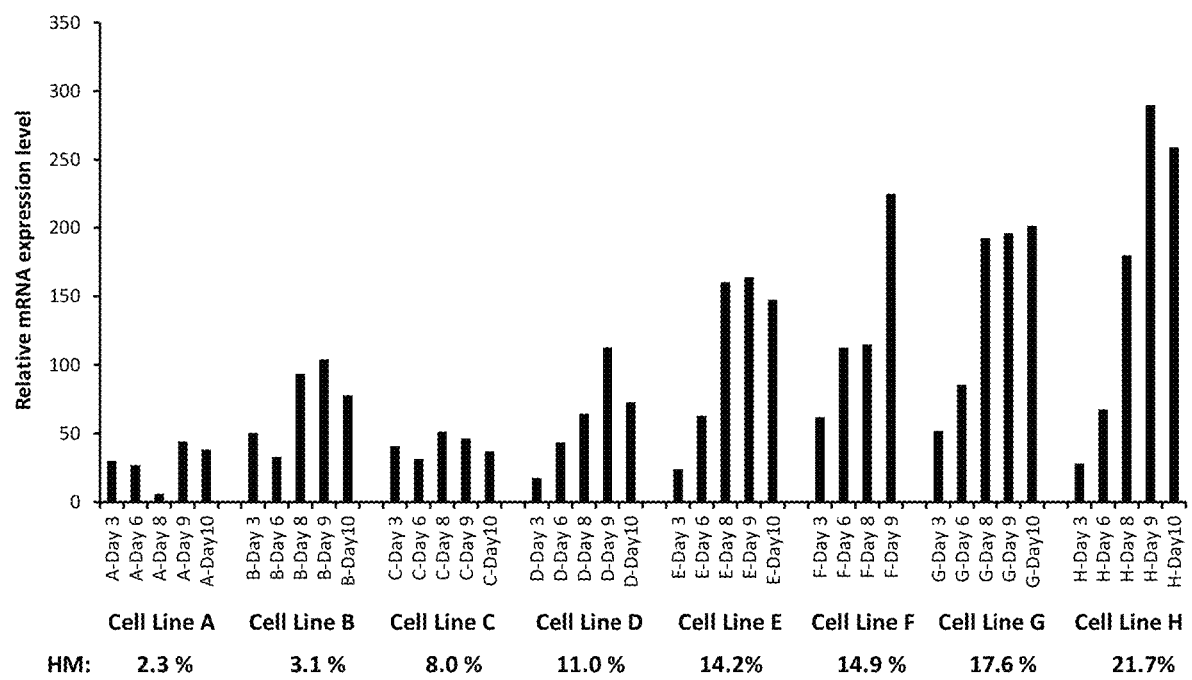
FIG. 4 The relative mRNA expression levels of arginase 1 from cell pellets collected from eight different cell lines on days 3, 6, 8, 9 and 10. The corresponding high mannose glycoform content is also shown.

Arginase 1, the enzyme that catalyzes the conversion of arginine to ornithine, was found to be up-regulated in cell lines with higher levels of high mannose, in a time-course dependent manner, see FIG. 4. This suggests that specific targeting with arginase inhibitors to block the activity of arginase and reduce the amount of ornithine production could be used to lower high mannose glycan levels.

Example 3

This example demonstrates the manipulation of the high mannose glycoform content of recombinant glycoproteins by regulating ornithine accumulation in the host cell expressing the recombinant glycoprotein is addressed.

Cell Lines, Cell Culture and Media

Cell lines H was used in this study. Cells were maintained in 3 L Erlenmeyer shake flasks (Corning Life Sciences, Lowell, Mass.) with 1 L working volume and cultivated under standard humidified condition at 36° C., 5% $CO_2$, and shaken at 70 rpm in an automatic $CO_2$ incubator (Thermo Fisher Scientific, Waltham, Mass.). Cells were sub-cultured in a selective growth media containing a 500 nM concentration of methotrexate (MTX) every four days, and subsequently transferred, inoculated and cultured in a growth media for four days before being seeded in a 24 wells plate for the experiments described below.

Small Scale Mock Perfusion

A modified mock perfusion in a 24 deep-well plate (Axygen, Union City, Calif.) was used to evaluate effects of spermine, arginine, ornithine and arginase concentrations on high mannose (HMN) modulation. An arginine-free formulation of a perfusion media was used for small scale mock perfusion Experiment #3 (arginine concentration studies) according to the experimental design. In small scale mock perfusion Experiment #4 all arginase inhibitors were added to a perfusion media. The four arginase inhibitors, BEC Hydrochloride, DL-α, Diflouromethylornithine Hydrochloride, $N^G$-Hydroxy-L-arginine Monoacetate salt and Nω-Hydroxy-nor-arginine diacetate salt, were purchased from EMD Millipore Corporation (Billerica, Mass.).

Briefly, the CHO cells were seeded in the plate at the targeted density ranging from 10-20×$10^6$ cells/mL with 3 mL working volume for each well. The cells were cultivated at 36° C., 5% $CO_2$, 85% relative humidity and shaken at 225 rpm in a 50-mm orbital diameter Kuhner incubator (Kuhner AG, Basel, Switzerland) for 3 or 4 days. Every 24 hours, the cells were centrifuged at 200×g for 5 minutes (Beckman Coulter, Brea, Calif.) to collect the spent media and each well was then replenished with 3 mL of fresh media. The collected spent media were analyzed for titer, key metabolites and % high mannose (% HMN) (when necessary). Cells were then harvested and cell counts and viability were measured.

Cell Growth, Metabolites and Antibody Titer Analysis

Viable cell density and viability were determined using a Cedex cell counter (Roche Innovative, Beilefed, Germany). Metabolites including glucose, lactate, ammonia, glutamine, glutamate were obtained from NovaBioprofile Flex (Nova Biomedical, Waltham, Mass.). Antibody concentration in the spent media was determined using a Affinity Protein A Ultra Performance liquid chromatography (UPLC) (Waters Corporation, Milford, Mass.) assay equipped with a 50 mm×4.6 mm i.d. POROS A/20 protein A column (Life Technologies, Carlsbad, Calif.). After the sample was injected, the column was washed by Phosphate-Buffered Saline (PBS) pH=7.1 to remove CHO host cell proteins. Bounded antibodies were then eluted in acidic PBS buffer (pH=1.9) and detected by UV absorbance at 280 nm to quantify antibody concentration.

HILIC Glycan Map

Different N-glycan species of antibodies were analyzed by hydrophilic-interaction liquid chromatography (HILIC). The purified antibodies were digested by N-glycosidase F (New England BioLabs, Ipswich, Mass.) at 37° C. for 2 hours to release the glycans. The released glycans were labeled with 2-aminobenzoic acid and cleaned up using GlycoClean S cartridges (Prozyme, Heyward, Calif.). Purified glycans were then desalted and reconstituted in water for assay. HILIC chromatography was performed with a 100 mm×2.1 mm i.d BEH Glycan column using UPLC (Waters Corporation, Milford, Mass.) and the eluted glycans were detected, identified, and qualified by a fluorescence detector based on different elution times of different glycans.

Small Scale Mock Perfusion Experiment #1: Spermine Concentration Study

Figure 5:
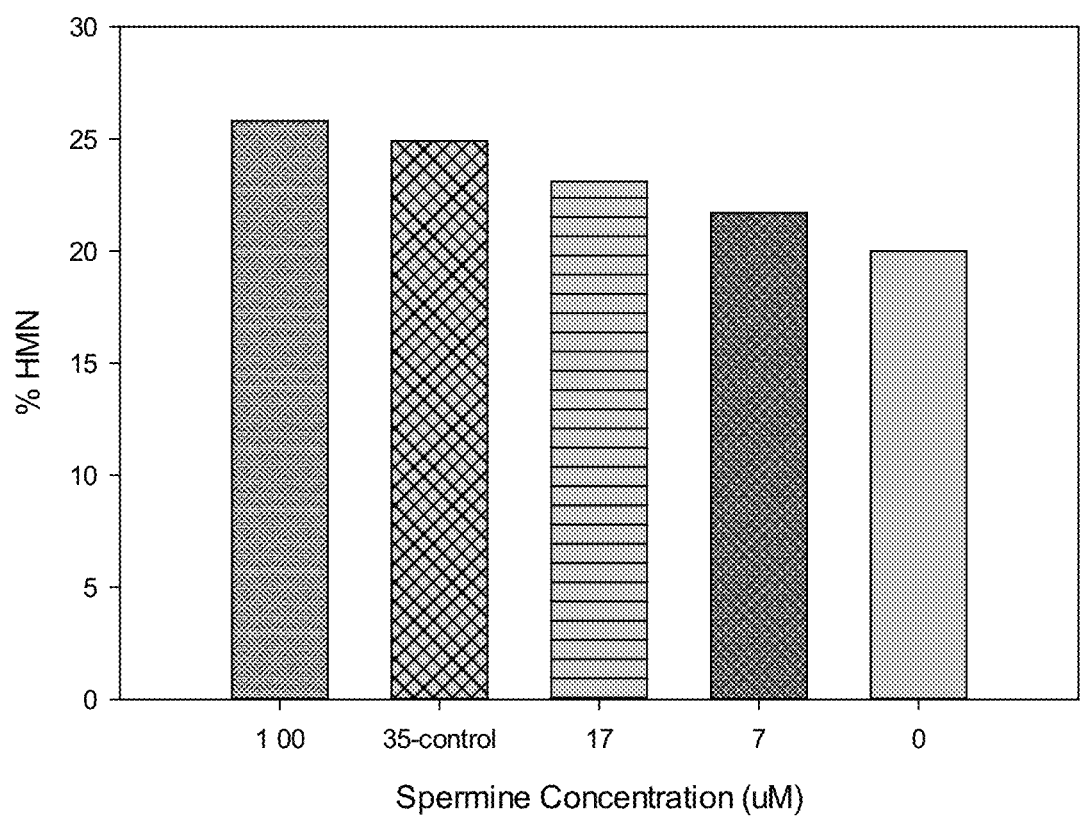
FIG. 5 High mannose glycoform content on recombinant glycoproteins expressed by cells grown in cell culture medium containing spermine tetrahydrochloride at concentrations of 0, 7, 17, 35 and 100 µM. Samples were collected on day 5 of the mock perfusion assay. The 35 µM sample served as a control.
Figure 6:
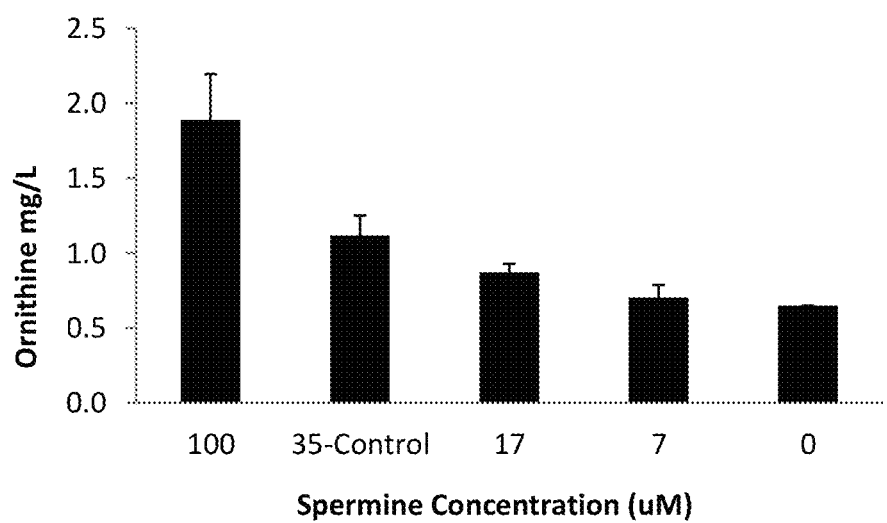
FIG. 6 Concentration of extracellular ornithine (mg/L) endogenously produced by cell cultures exposed to spermine tetrahydrochloride at concentrations of 0, 7, 17, 35 and 100 µM. Samples were collected on day 5 of the mock perfusion assay. The 35 µM sample served as a control.

Five different concentrations of spermine were tested in this study. Perfusion cell culture media containing 0, 7, 17, 35 and 100 μM spermine tetrahydrochloride (spermine 4HCl) were tested. The perfusion medium containing 35 μM spermine acted as a control. The results from day 5 samples show that as the spermine concentration was reduced, the % HMN decreased, see FIG. 5. Titer was not affected by reduction/depletion of spermine. Reduction of HM level was achieved through reduction in ornithine level when the amount of spermine was reduced in the media. As shown in FIG. 6, the amount of ornithine decreased with a decrease in spermine concentration.

Small Scale Mock Perfusion Experiment #2: Ornithine Concentration Study

Figure 7:
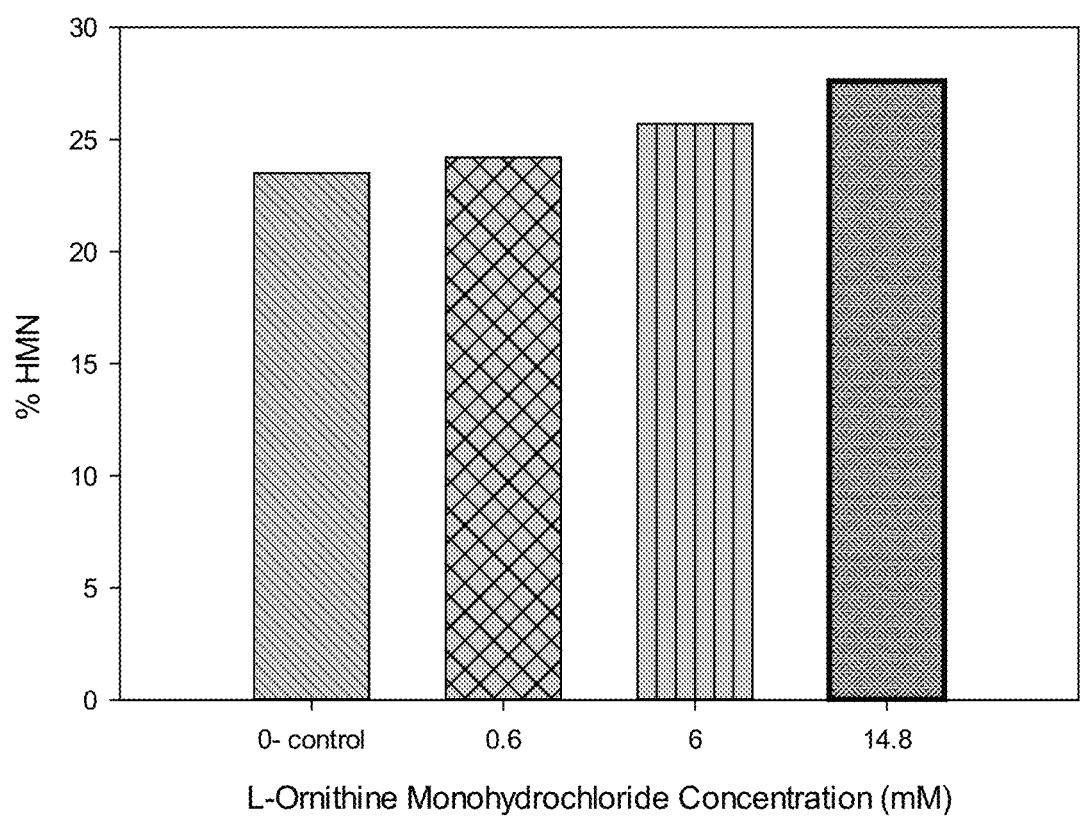
FIG. 7 High mannose glycoform content on recombinant glycoproteins expressed by cells grown in cell culture medium containing L-ornithine monohydrochloride at concentrations of 0, 0.6, 6 and 14.8 mM. Samples were collected on day 5 of the mock perfusion assay. The 0 mM sample served as a control.

Four different concentrations of L-ornithine monohydrochloride were tested. Perfusion cell culture media containing 14.8, 6, 0.6 and 0 (control) mM L-ornithine monohydrochloride (Sigma-Aldrich, St. Louis, Mo.) were used. The results showed that as the ornithine concentration was increased, the % HMN increased, see FIG. 7. A second experiment was performed using Cell Line I in 2 L bioreactors. Cell line I expresses an IgG2 antibody and was grown under fed-batch conditions. In one bioreactor, the media received a single supplement of 0.1 g/L L-ornithine monohydrochloride on day 0 of the culture, the second bioreactor acted as an ornithine-free control. The cultures were maintained from 12 days in cell culture media containing soy-hydrolysates. Bolus feed medium containing soy hydrolysates was fed on days 4 and 8.

Glycan profiling was performed by peptide mapping. The antibody was digested by trypsin with a method similar to described by Ren et al. (2009) Anal. Biochem. 392 12-21).

Specifically, about 50-70 µg of each antibody was denatured and reduced with 7.0 M guanidine.HCl, 6 mM dithiothreitol (DTT) in 0.2 M tris buffer (pH 7.5) at 37° C. for 30 minutes. Each denatured/reduced sample was alkylated with 14 mM iodoacetic acid at 25° C. for 25 minutes, followed by quenching the reaction by adding 8 mM DTT. The reduced/ alkylated antibody samples were then exchanged into a 0.1 M tris buffer at pH 7.5 with a Pierce detergent removal spin column (Thermo Fisher Scientific Inc., Rockford, Ill.) according to manufacturer suggested protocol. The buffer-exchanged sample was incubated at 37° C. with 3.5 µg trypsin for 60 minutes. Digestion was quenched by adding 2.2 µL of 10% acetic acid. About 12-17 µg of digested antibody was injected for analysis.

The digested antibody was analyzed using an Agilent 1260 HPLC system directly connected to a Thermo Scientific LTQ-Orbitrap Elite mass spectrometer (Thermo Fisher Scientific Inc., Rockford, Ill.). Proteolytic peptides were separated on a Waters BEH 300 C18 column (Waters Corporation, Milford, Mass.) 2.1×150 mm, 1.7µ particle at 40° C. with a flow rate of 0.2 mL/min. Mobile phase A was 0.02% TFA in water and mobile phase B was 0.018% TFA in acetonitrile. Peptides were eluted with a gradient of 0.5-40% B in 90 minutes, followed by column washing and re-equilibration. Mass spectrometer was set up for a full MS scan in the orbitrap with 120,000 resolution followed by five data-dependent CID MS/MS scans in the linear trap with dynamic exclusion. Automated data analysis for glycan profiling was performed using MassAnalyzer (see Zhang, (2009) Analytical Chemistry 81: 8354-8364).

Figure 8:
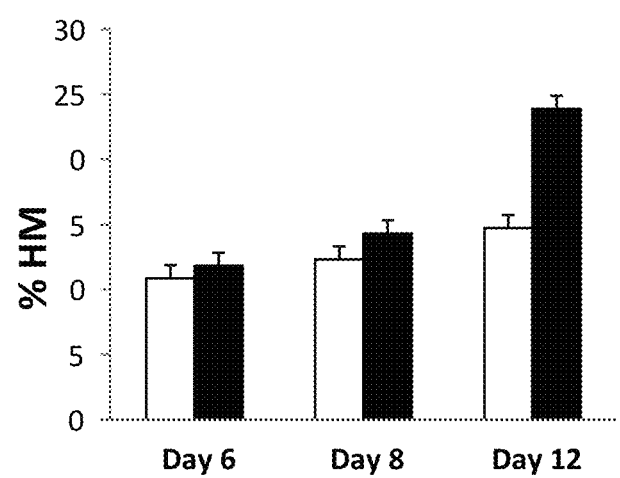
FIG. 8 High mannose glycoform content on recombinant glycoproteins expressed by Cell line "I" grown in cell culture medium containing 0.1 g/L L-ornithine monohydrochloride (black bars) or control cell culture containing no exogenously added ornithine (white bars). Samples were collected on days 6, 8 and 12.

The results again show that as the ornithine concentration is increased the % HMN increased, see FIG. 8.

Small Scale Mock Perfusion Experiment #3: Arginine Concentration Study

Figure 9:
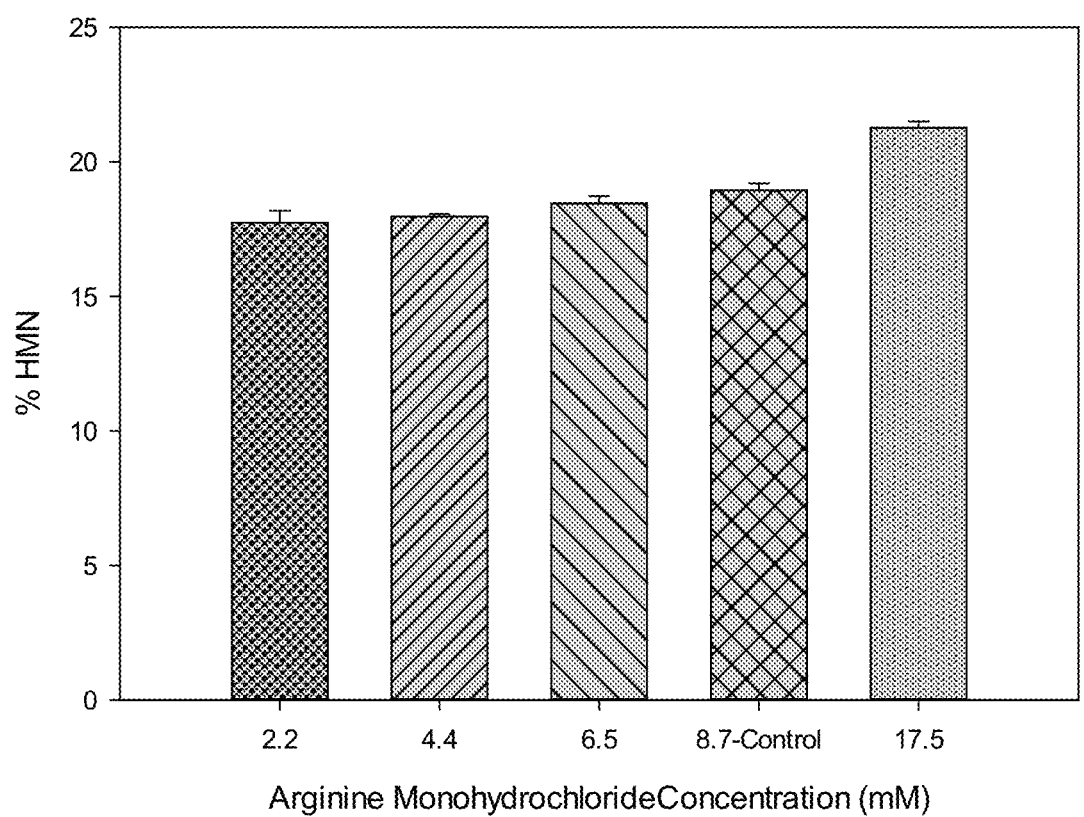
FIG. 9 High mannose glycoform content on recombinant glycoproteins expressed by cells grown in cell culture medium containing arginine monohydrochloride at concentrations of 2.2, 4.4, 6.5, 8.7 and 17.5 mM. The 8.7 mM sample acted as control. Samples were collected on day 4 of the mock perfusion assay.

Five different concentrations of arginine were tested in this study. Perfusion cell culture media containing 3.686, 1.38, 0.92 and 0.46 g/L arginine were tested. The perfusion medium containing 1.843 g/L arginine was used as a control. The results show that as the arginine concentration is increased the % HM increased, see FIG. 9.

Small Scale Mock Perfusion Experiment #4: Arginase Inhibitor Studies

Figure 10:
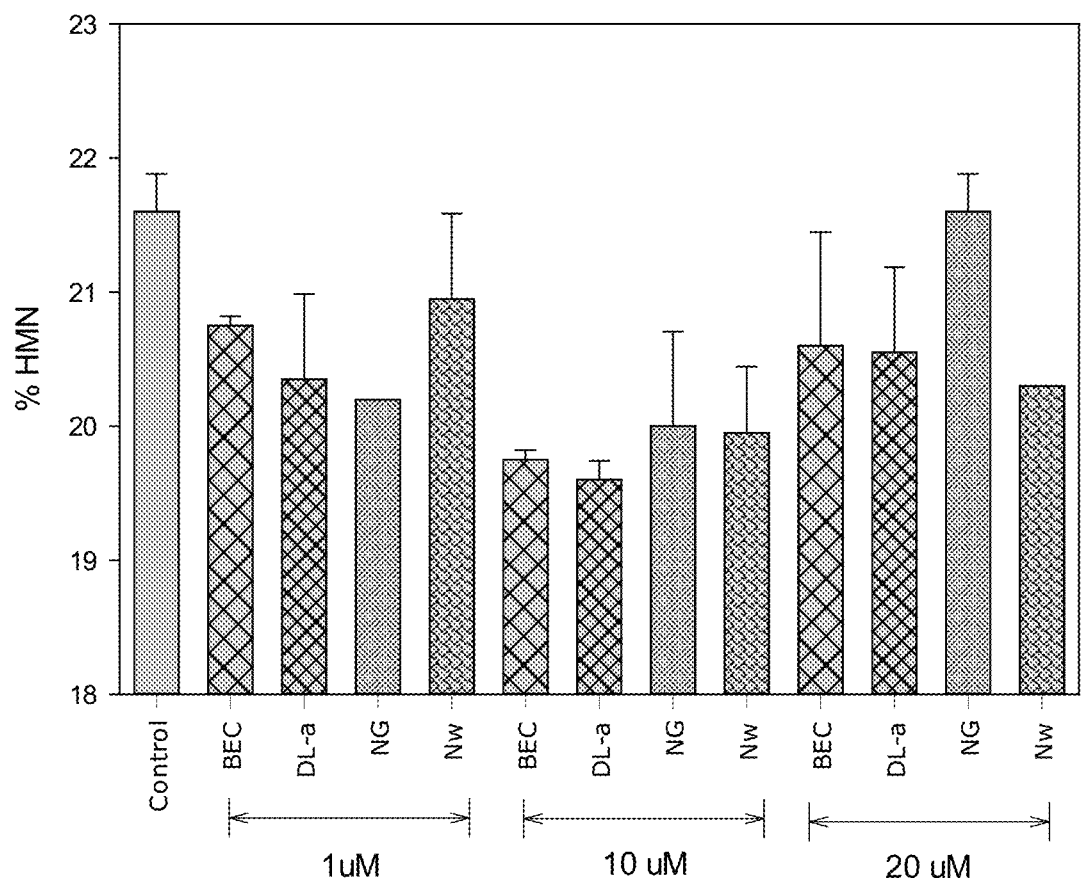
FIG. 10 High mannose glycoform content on recombinant glycoproteins expressed by cells grown in cell culture medium supplemented with various arginase inhibitors: BEC Hydrochloride (BEC), DL-α, Diflouromethylornithine Hydrochloride (DL-a), $N^G$-Hydroxy-L-arginine Monoacetate salt (NG) and Nω-Hydroxy-nor-arginine diacetate salt (Nw) at concentrations of 1, 10 and 20 µM. Control contained no inhibitor. Samples were collected on day 4 of the mock perfusion assay.

Two series of arginase inhibitor experiments were conducted. In the first series of experiments, four commercially available arginase inhibitors BEC Hydrochloride, DL-α, Diflouromethylornithine Hydrochloride, $N^G$-Hydroxy-L-arginine Monoacetate salt and Nω-Hydroxy-nor-arginine diacetate salt were added to the cell cultures at three different concentrations, 1, 10 and 20 µM. The control was inhibitor free. From this experiment it was concluded the inhibitors BEC and DL-α were most effective in decreasing % HM (FIG. 10).

Figure 11:
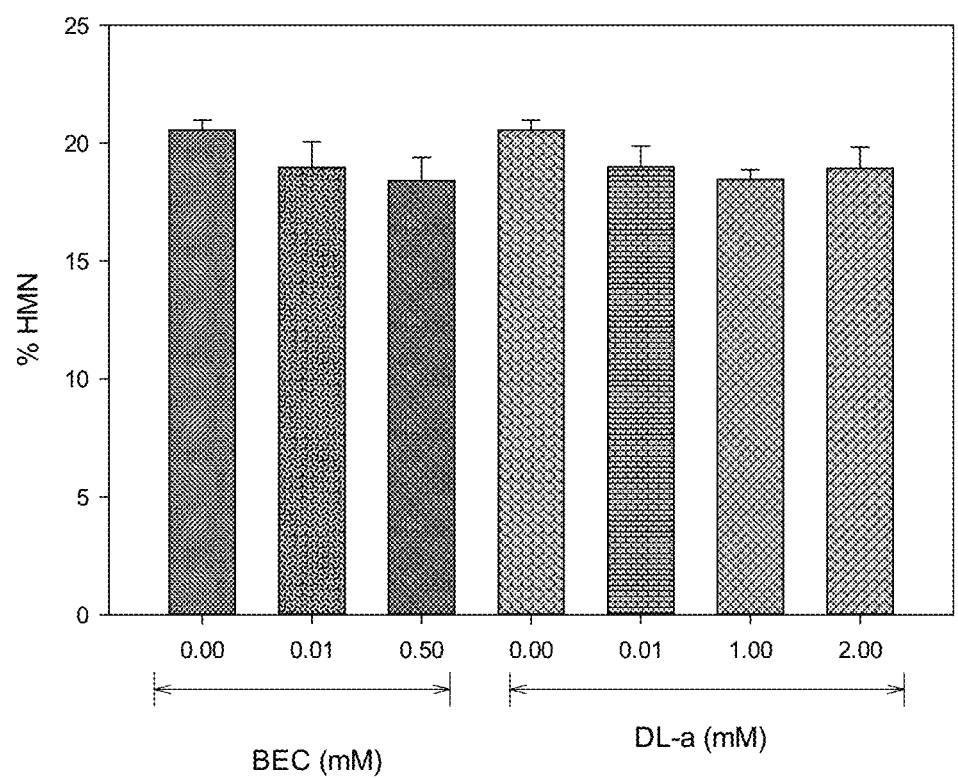
FIG. 11 High mannose glycoform content on recombinant glycoproteins expressed by cells grown in cell culture medium containing the arginase inhibitor BEC Hydrochloride (BEC) at concentrations of 0.0 0.01 and 0.5 mM and, DL-α, Diflouromethylornithine Hydrochloride (DL-a) at concentrations of 0.0, 0.01, 1.0 and 2.0 mM. Samples were collected on day 4 of the mock perfusion assay.

A second series experiments were conducted using the BEC and DL-α inhibitors. The BEC inhibitor was tested at 0 (control), 10 µM and 0.5 mM concentrations in perfusion cell culture media. The DL-α inhibitors was tested at 0 (control), 10 µM, 1.0 mM and 2.0 mM concentrations in perfusion culture media. It was demonstrated that % HM was decreased as both inhibitor concentrations increased, see FIG. 11.

What is claimed is:

1. A method of increasing high mannose glycoform content of a recombinant protein comprising culturing a host cell expressing the recombinant protein in a cell culture comprising ornithine or arginine, wherein ornithine production in the host cell is increased when compared to the host cell expressing the recombinant protein is cultured in a cell culture lacking ornithine or arginine, and the recombinant protein has an increased high mannose glycoform content than when the recombinant protein is expressed in the cell culture lacking ornithine or arginine.

2. The method of claim 1, wherein ornithine accumulation in the host cell is increased by the addition of at least 0.6 mM ornithine to the cell culture.

3. The method of claim 1, wherein the concentration of ornithine is selected from the group consisting of 0.6 to 14.8 mM; 6 to 14.8 mM; 0.6 mM, 6 mM, and 14.8 mM.

4. The method of claim 1, wherein ornithine accumulation in the host cell is regulated by the addition of at least 8.7 mM arginine to cell culture medium.

5. The method of claim 1, wherein the concentration of arginine is selected from the group consisting of 8.7 mM to 17.5 mM; 8.7 mM; and 17.5 mM.

6. The method of claim 1, wherein the host cell expressing the recombinant protein is cultured in a batch culture, fed-batch culture, perfusion culture, or combinations thereof.

7. The method of claim 1, wherein the host cell expressing the recombinant protein is cultured in a bioreactor.

8. The method of claim 7, wherein the bioreactor has a capacity selected from the group consisting of at least 500 L; 500 L to 2000 L; and 1000 L to 2000 L.

9. The method of claim 1, wherein the host cell expressing the recombinant protein is cultured in a serum-free cell culture medium.

10. The method of claim 9, wherein the serum-free culture medium is a perfusion cell culture medium.

11. The method of claim 1, wherein the host cells are mammalian cells.

12. The method of claim 1, wherein the host cells are Chinese Hamster Ovary (CHO) cells.

13. The method of claim 1, wherein the recombinant protein is a glycoprotein.

14. The method of claim 1, wherein the recombinant protein is selected from the group consisting of a human antibody, a humanized antibody, a chimeric antibody, a recombinant fusion protein, or a cytokine.

15. The method of claim 1, further comprising a step of harvesting the recombinant protein produced by the host cell.

16. The method of claim 1, wherein the recombinant protein produced by the host cell is purified and formulated into a pharmaceutically acceptable formulation.

* * * * *